United States Patent
Sebhat et al.

(10) Patent No.: US 7,880,014 B2
(45) Date of Patent: Feb. 1, 2011

(54) ANGIOTENSIN II RECEPTOR ANTAGONISTS

(75) Inventors: Iyassu K. Sebhat, Jersey City, NJ (US); Michael Man-chu Lo, Edison, NJ (US); Ravi P. Nargund, East Brunswick, NJ (US); Amjad Ali, Freehold, NJ (US); Chris Franklin, Keasbey, NJ (US); Nicoletta Almirante, Milan (IT); Laura Storoni, Cesano Maderno (IT); Silvia Stefanini, San Donato Milanese (IT)

(73) Assignees: Merck Sharp & Dohme Corp., Rahway, NJ (US); NiCox S.A., Valbonne (FR)

( * ) Notice: Subject to any disclaimer, the term of this patent is extended or adjusted under 35 U.S.C. 154(b) by 26 days.

(21) Appl. No.: 12/000,247

(22) Filed: Dec. 11, 2007

(65) Prior Publication Data

US 2008/0194660 A1    Aug. 14, 2008

Related U.S. Application Data

(60) Provisional application No. 60/874,630, filed on Dec. 13, 2006.

(51) Int. Cl.
C07D 257/00    (2006.01)
C07D 403/00    (2006.01)

(52) U.S. Cl. .................................. 548/250; 548/300.1

(58) Field of Classification Search ............... 548/250, 548/300.1
See application file for complete search history.

(56) References Cited

U.S. PATENT DOCUMENTS

| | | | |
|---|---|---|---|
| 5,138,069 A | 8/1992 | Carini et al. | |
| 5,153,197 A | 10/1992 | Carini et al. | |
| 6,242,432 B1 * | 6/2001 | del Soldato | 514/89 |
| 7,186,753 B1 * | 3/2007 | Del Soldato | 514/509 |

FOREIGN PATENT DOCUMENTS

| | | |
|---|---|---|
| WO | WO-92/01668 | 2/1992 |
| WO | WO-00/61537 | 10/2000 |
| WO | WO-00/61541 | 10/2000 |
| WO | WO-01/12584 | 2/2001 |
| WO | WO-2005/011646 | 2/2005 |
| WO | WO-2005/023182 | 3/2005 |
| WO | WO-2005/070868 | 8/2005 |
| WO | WO-2006/079610 | 8/2006 |

\* cited by examiner

*Primary Examiner*—Susannah Chung
(74) *Attorney, Agent, or Firm*—Covington & Burling LLP; Paul J. Berman; Melody Wu

(57) ABSTRACT

A compound having the structure

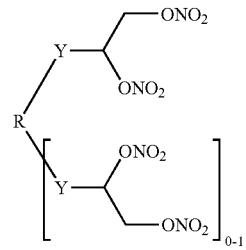

wherein R is an angiotensin receptor antagonist active group, Y is -$Y^1$-$Y^2$-$Y^3$-$Y^4$-$Y^5$-; $Y^1$ is $C(R^1R^2)$; $R^1$ is selected from the group consisting of hydrogen and $C_{1-4}$ alkyl; $R^2$ is selected from the group consisting of hydrogen, $C_{1-4}$ alkyl, and —OC(O)$C_{1-4}$ alkyl; $Y^2$ is O or $CH_2$; $Y^3$ is C(O) or $CH_2$; $Y^4$ is O or $CH_2$; $Y^5$ is —$(CH_2)_{1-2}$—$(X)_{0-1}$—$(CH_2)_{0-1}$— or is absent; X is —O— or —$CR^3R^4$—; and $R^3$ and $R^4$ are independently selected from the group consisting of hydrogen and $C_1$-$C_4$ alkyl; or a pharmaceutically acceptable salt or hydrate thereof, which is useful for treating hypertension.

7 Claims, No Drawings

ANGIOTENSIN II RECEPTOR ANTAGONISTS

BACKGROUND OF THE INVENTION

U.S. Pat. No. 5,138,069 generically and specifically describes 2-butyl-4-chloro-1-[p-(o-1H-tetrazol-5-ylphenyl)-benzyl]imidazole-5-methanol potassium salt and 2-butyl-4-chloro-1-[(2'-1H-tetrazol-5-yl)biphenyl-4-yl)methyl]imidazole-5-carboxylic acid. Columns 261-263 of U.S. Pat. No. 5,138,069 describe general procedures for formulating compounds described in the patent, including capsules, tablets, injection formulations, and suspensions. U.S. Pat. No. 5,153,197, describes the use of these compounds, alone and in combination with a diuretic, to treat a patient having hypertension.

WO2005011646 describes angiotensin II receptor blocker nitroderivatives, pharmaceutical compositions containing them and their use for the treatment of cardiovascular, renal and chronic liver diseases, inflammatory processes and metabolic syndromes. The publication describes a variety of angiotensin receptor blocker compounds each of which are covalently linked in a variety of ways to a nitric oxide group. Specific examples include angiotensin receptor blockers with one covalently-linked nitric oxide group, and angiotensin receptor blockers with two independently-covalently-linked nitric oxide groups.

WO2005023182 describes nitrosated and nitrosylated cardiovascular compounds, and compositions comprising at least one nitrosated and nitrosylated cardiovascular compound and optionally at least one nitric oxide donor. The cardiovascular compound which is nitrosated or nitrosylated may be an aldosterone antagonist, an angiotensin II receptor antagonist, a calcium channel blocker, an endothelin antagonist, a hydralazine compound, a neutral endopeptidase inhibitor or a renin inhibitor. The nitric oxide donor may be selected from S-nitrosothiols, nitrites, nitrates, N-oxo-N-nitrosamines, furoxans, and sydnonimines.

WO2005070868 describes combination therapy for treating cyclooxygenase-2 mediated diseases or conditions at risk of thrombotic cardiovascular events which involves administering selected cyclooxygenase-2 inhibitor in combination with a nitric oxide donating compound such as 5,6-bis(nitrooxy)hexyl acetate, 6-hydroxyhexane-1,2-diyl dinitrate, 5-hydroxypentane-1,2-diyl dinitrate, (5R)-5,6-bis(nitrooxy) hexyl 4-nitrobenzoate, (5S)-5,6-bis(nitrooxy)hexyl 4-nitrobenzoate, (2R)-6-hydroxyhexane-1,2-diyl dinitrate, (2S)-6-hydroxyhexane-1,2-diyl dinitrate, (2S)-propane-1,2-diyl dinitrate, and (2R)-propane-1,2-diyl dinitrate.

SUMMARY OF THE INVENTION

The present invention includes angiotensin II receptor antagonist bis(nitrooxy) derivatives, including 2-butyl-4-chloro-1-[(2'-(1-H-tetrazol-5-yl)biphenyl-4-yl)methyl]-imidazole-5-carboxylate bis(nitrooxy) derivatives, including various pharmaceutically acceptable salts and hydrates of these forms, and pharmaceutical formulations for controlled and sustained delivery of these forms to a patient.

The salts include non-toxic salts such as those derived from inorganic acids, e.g. hydrochloric, hydrobromic, sulfuric, sulfamic, phosphoric, nitric and the like, or the quaternary ammonium salts which are formed, e.g., from inorganic or organic acids or bases. EXAMPLEs of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The invention also includes a method for treating hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, by administering an angiotensin II receptor antagonist of the invention to a patient having one or more of these conditions.

DETAILED DESCRIPTION OF THE INVENTION AND PREFERRED EMBODIMENTS

Compounds of the invention are angiotensin II receptor antagonist bis(nitrooxy) derivatives having the general formula:

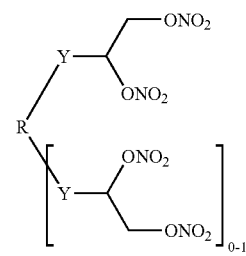

wherein R is selected from the group consisting of

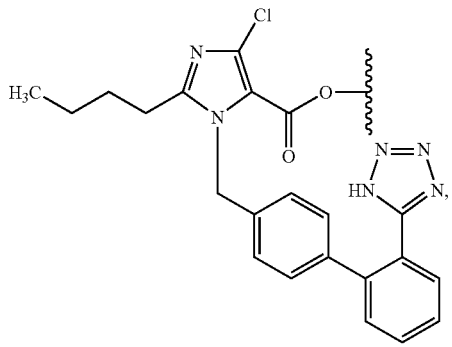

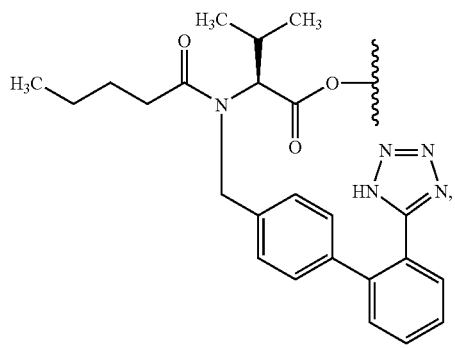

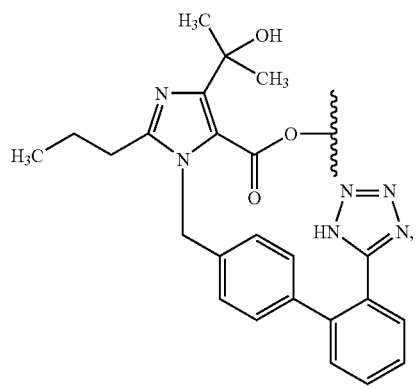

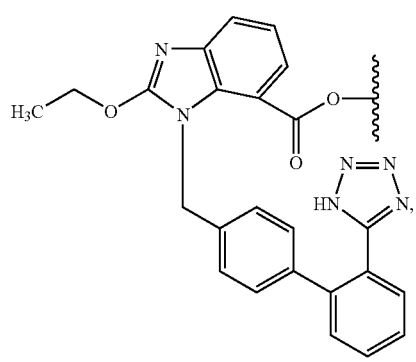

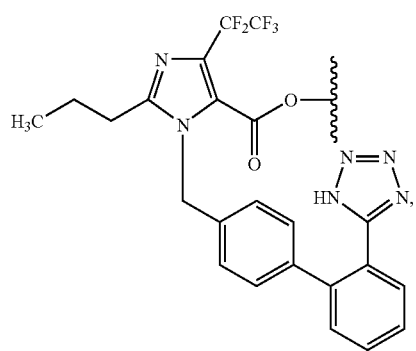

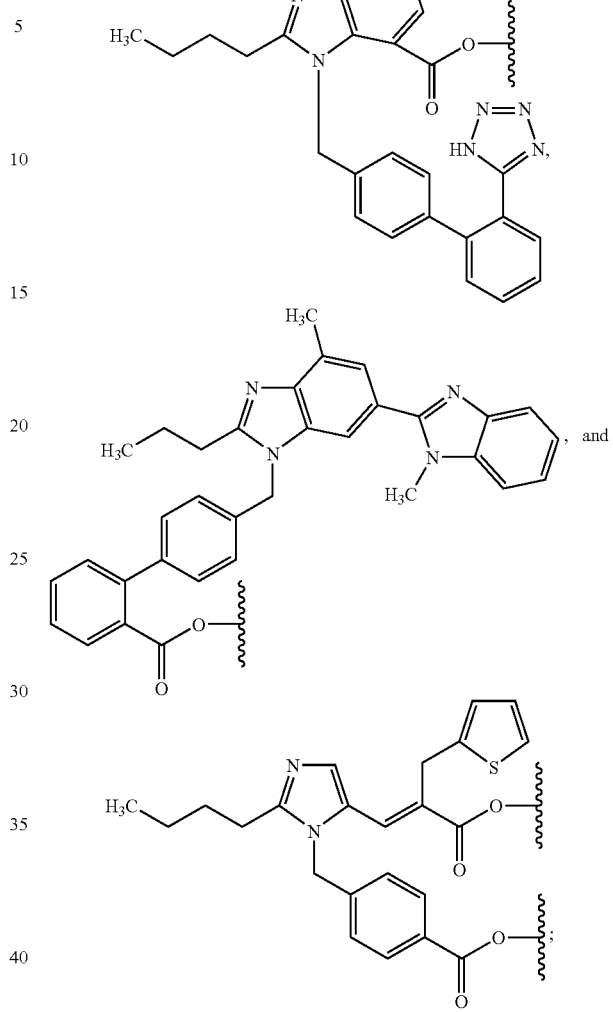

Y is -Y$^1$-Y$^2$-Y$^3$-Y$^4$-Y$^5$-;

Y$^1$ is C(R$^1$R$^2$);

R$^1$ is selected from the group consisting of hydrogen and C$_{1-4}$ alkyl;

R$^2$ is selected from the group consisting of hydrogen, C$_{1-4}$ alkyl, and —OC(O)C$_{1-4}$ alkyl;

Y$^2$ is O, C(O), P(O)(OH) or CH$_2$, provided that when Y$^3$ is P(O)(OH), then Y$^2$ is O;

Y$^3$ is O, C(O), P(O)(OH) or CH$_2$, provided that when Y$^2$ is C(O), then Y$^3$ is not C(O), and further provided that when Y$^2$ is O, then Y$^3$ is not O, and when Y$^2$ is P(O)(OH), then Y$^3$ is O;

Y$^4$ is O or CH$_2$ or is absent, provided that when Y$^3$ is O, then Y$^4$ is not O;

Y$^5$ is —(CH$_2$)$_{1-2}$—(X)$_{0-1}$—(CH$_2$)$_{0-1}$— or is absent;

X is —O— or —CR$^3$R$^4$—; and

R$^3$ and R$^4$ are independently selected from the group consisting of hydrogen and C$_1$-C$_4$ alkyl;

or a pharmaceutically acceptable salt thereof.

In one embodiment, Y$^2$ is O or C(O), and all other variables are as previously defined.

In another embodiment, Y$^3$ is C(O), Y$^2$ is O, and all other variables are as previously defined.

In another embodiment, Y is —C(R¹R²)—O—C(O)—Y⁴—Y⁵—, and all other variables are as previously defined.

In another embodiment, the compound has the structure

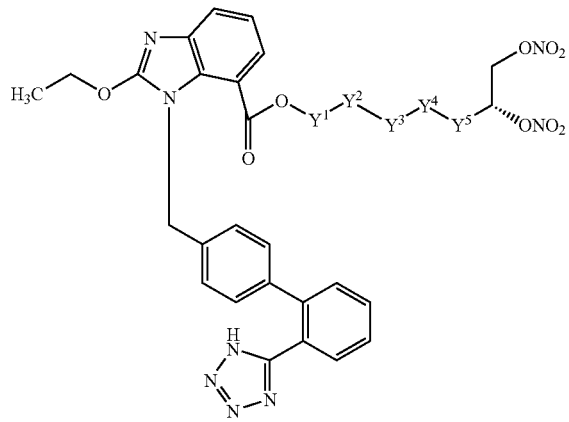

and all variables are as previously defined.

In another embodiment, the compound has the structure

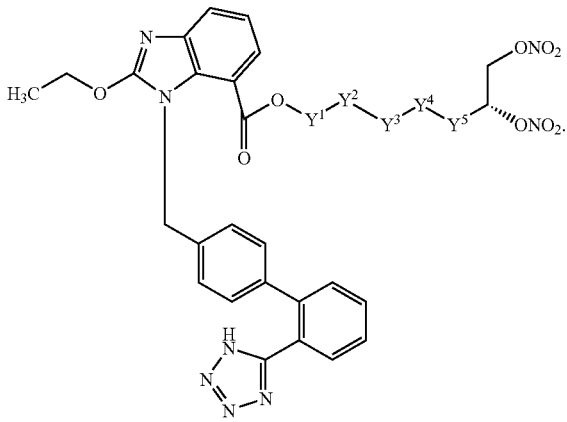

wherein $Y^1$ is $C(CH_3)_2$, $Y^2$ is O, $Y^3$ is C(O), $Y^4$ is O and $Y^5$ is —$(CH_2)_{1-2}$—$(X)_{0-1}$—$(CH_2)_{0-1}$, wherein X is —O— or —$CR^3R^4$—; and $R^3$ and $R^4$ are independently selected from the group consisting of hydrogen and $C_1$-$C_4$ alkyl;

or a pharmaceutically acceptable salt or hydrate thereof.

In another embodiment, the compound is selected from the group consisting of

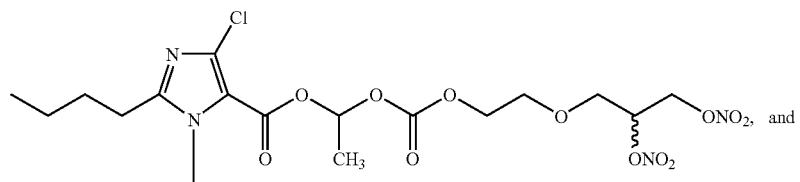

and

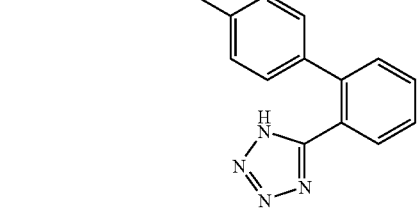

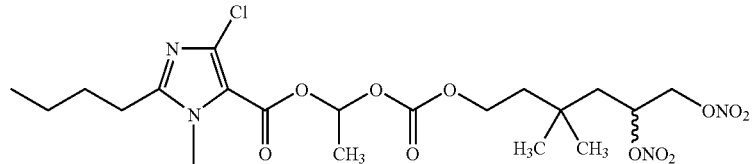

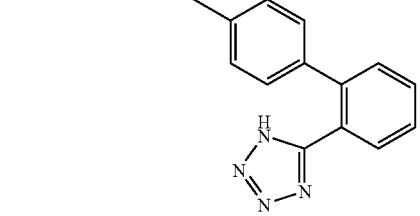

or a pharmaceutically acceptable salt thereof.

In another embodiment, the compound is selected from the group consisting of
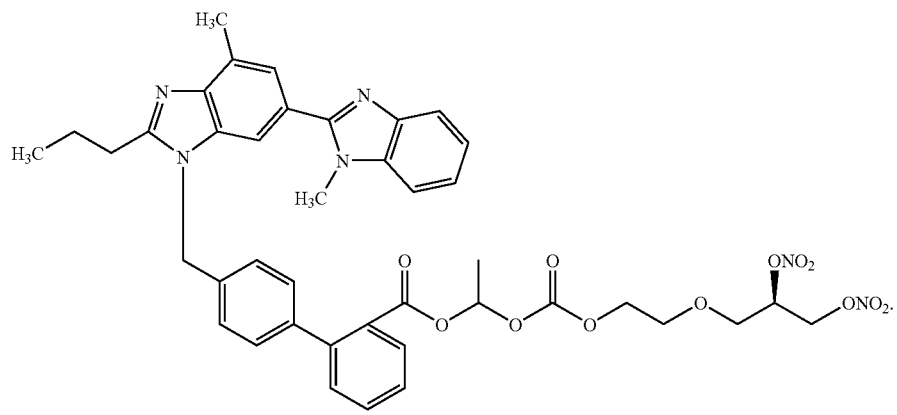
In another embodiment, the compound is selected from the group of compounds (i) to (xix) shown below:
TABLE (i) - (xvi)
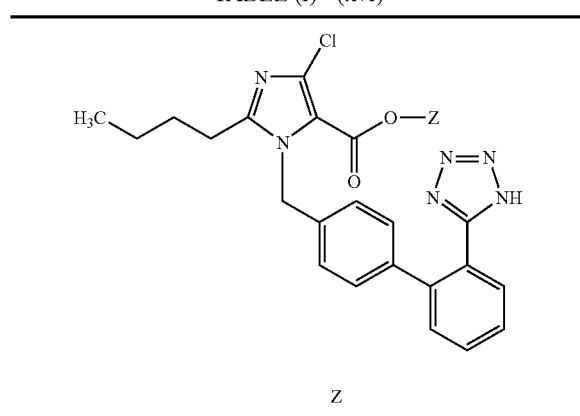
Z
i) 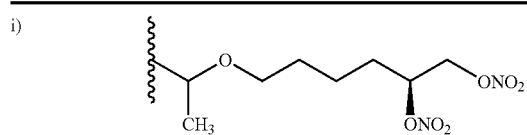
ii) 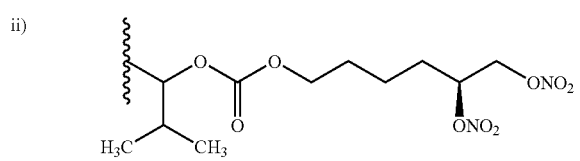
iii) 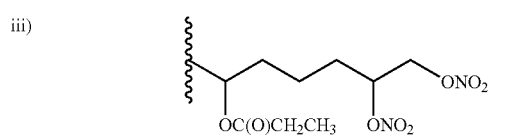
iv) 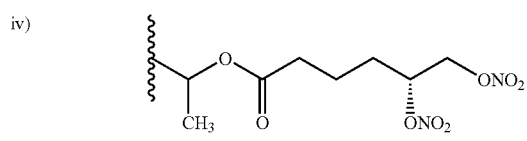
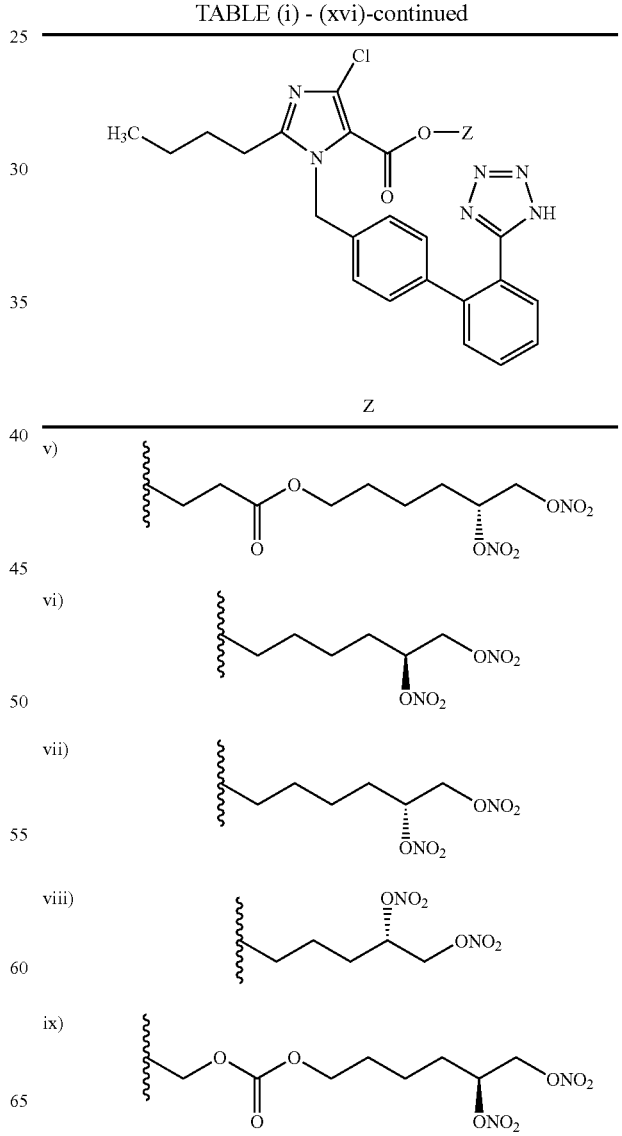

TABLE (i) - (xvi)-continued
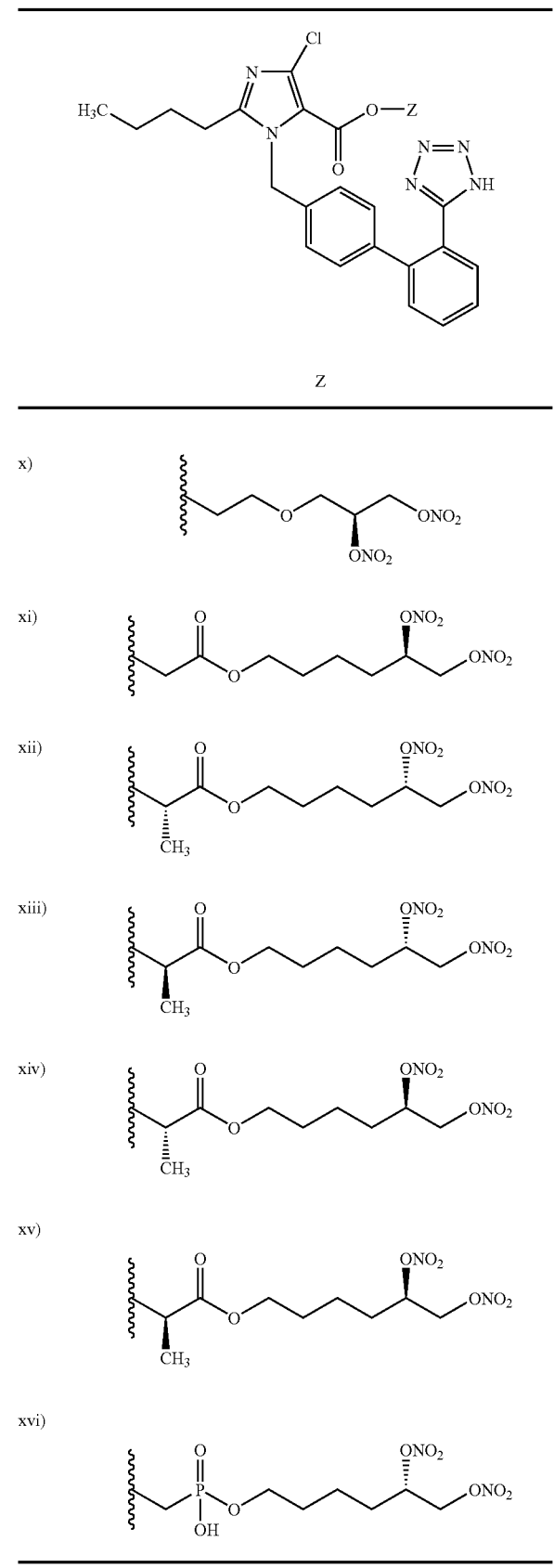
TABLE (xvii) - (xxiv)
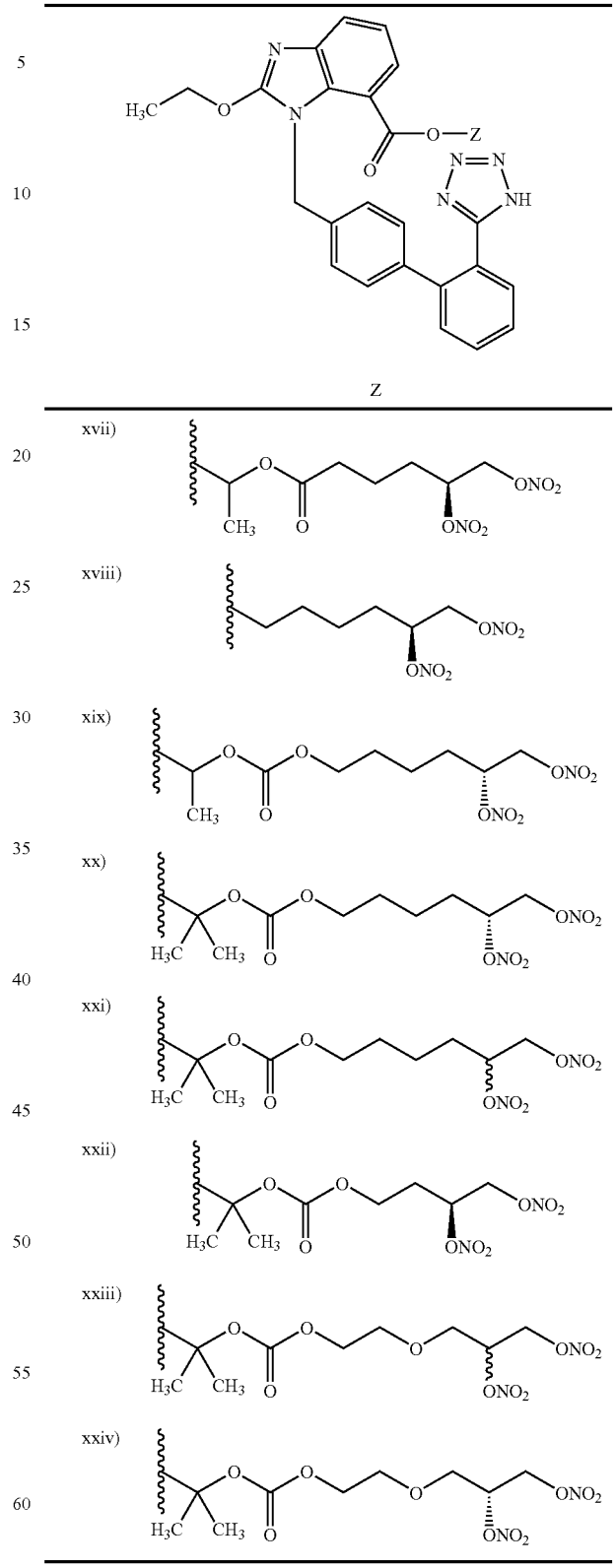
In another embodiment, the compounds of the invention are angiotensin II receptor antagonist bis(nitrooxy) 2-butyl-4-chloro-1-[(2'-(1-H-tetrazol-5-yl)biphenyl-4-yl)methyl]-imidazole-5-carboxylates, having the structure

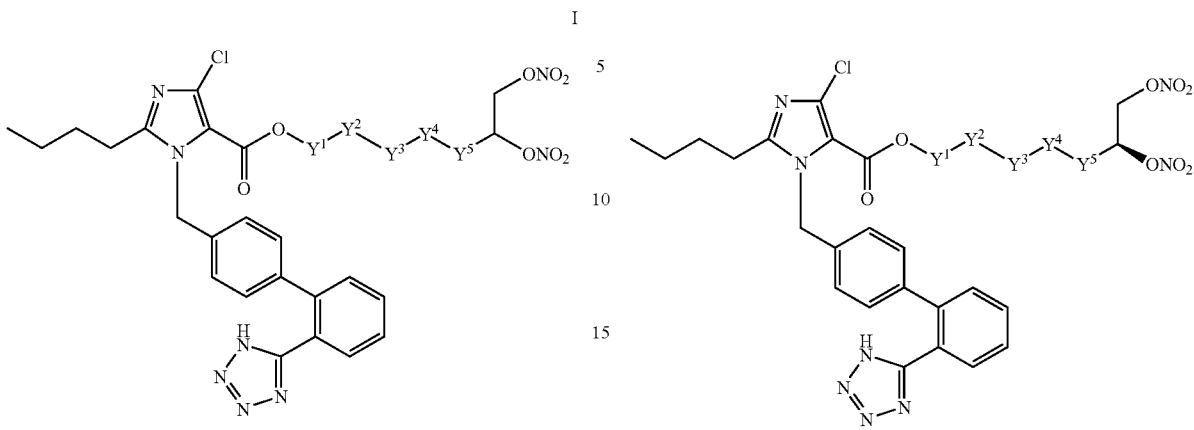

or a pharmaceutically acceptable salt thereof, wherein $Y^1$ is $CH(CH_3)$ or $CH_2$, $Y^2$ is O or $CH_2$, $Y^3$ is C(O) or $CH_2$, $Y^4$ is O or $CH_2$, and $Y^5$ is $(CH_2)_{2-4}$ or is absent.

In another embodiment, the compound has the structure

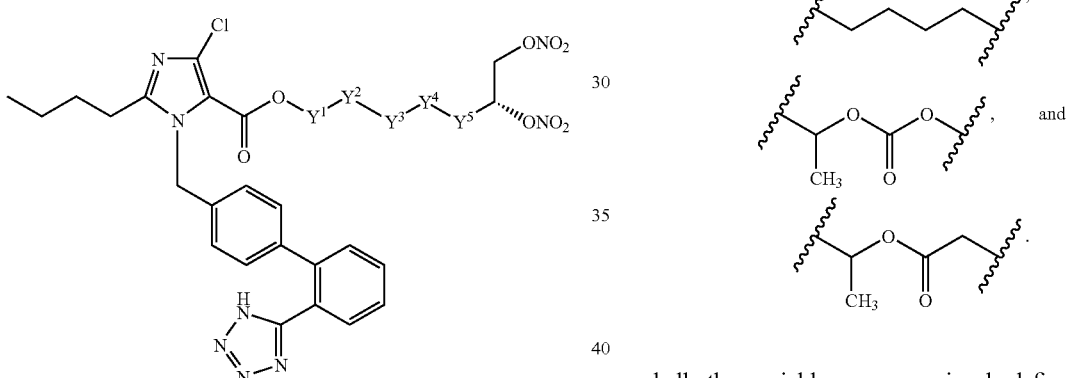

and all variables are as previously defined.

In another embodiment, the compound has the structure and all variables are as previously defined.

In another embodiment, $-Y^1-Y^2-Y^3-Y^4-$ is selected from the group consisting of and all other variables are as previously defined.

In another embodiment, $Y^5$ is $(CH_2)_2$, $(CH_2)_4$, or is absent.

In another embodiment, the compound is selected from the group consisting of

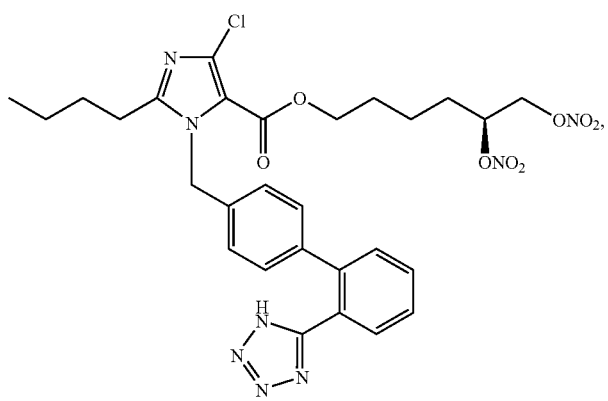

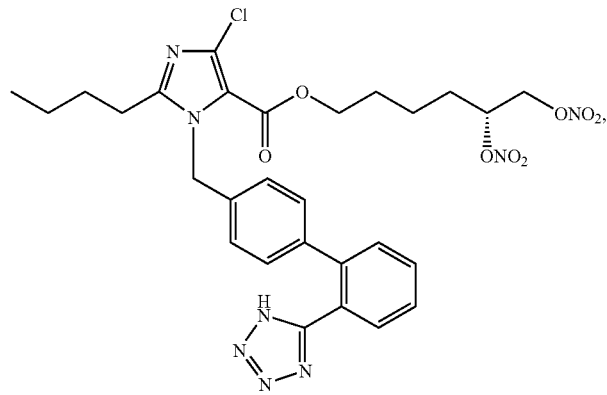

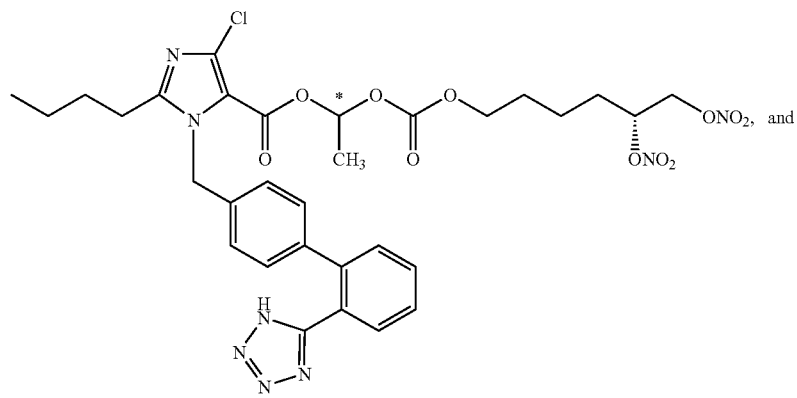

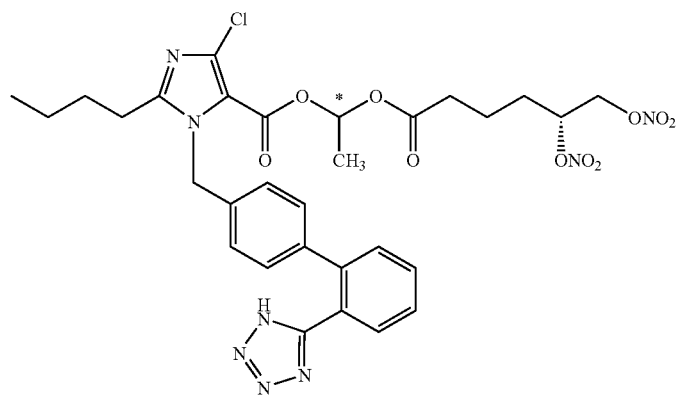

or a pharmaceutically acceptable salt thereof.

In another embodiment, the compound is selected from the group consisting of

1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate—Diastereomer A, and 1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate—Diastereomer B.

In another embodiment, the compound is 1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate—Diastereomer A.

The compounds of the present invention may have one or two chiral centers, providing for up to two ((R) and (S)) or four (R,R), (S,S), (R,S), and (S,R) stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. The structure marking "*" indicates the location of a carbon atom that is a chiral center.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

The dinitrate compounds of the invention provide enhanced NO release over mononitrate analogs. While mononitrate compounds orally dosed to rats result in reactive nitrite species circulating in plasma with maximal concentration in the 0.5-2.8 µM range, similar dosing of compounds of the present invention result in an unexpectedly large increase in circulating nitrite concentrations. A consideration of stoichiometry leads to an expectation of a doubling of nitrite levels. Compounds of the invention, however, provide a nitrite level increase more than two fold. Also, in vitro, tissue-based measure of vessel relaxation, determined in rabbit aortic slices, show large improvements in $EC_{50}$ (molar concentration of compound which produces 50% of the maximum possible response for that compound) compared to mononitrates which are greater than the increase expected based on the stoichiometric relationship.

Biochemical evidence for the generation of NO in vivo in response to test compound administration was obtained from studies in Sprague-Dawley (SD) rats. Administration of test compound to fasted SD rats (40 mpk, PO) results in the appearance of reactive nitrogen species (RNS), assessed using the diaminonapthalene derivitization (DAN) assay. Compounds 1-3 as numbered and identified in Data Table 1 below were tested, compounds 2 and 3 showed improved RNS levels and improved $EC_{50}$ values in vessel relaxation assay.

DATA TABLE 1

| Structure | Compound Number | $EC_{50}$ in vessel relaxation assay |
|---|---|---|
| 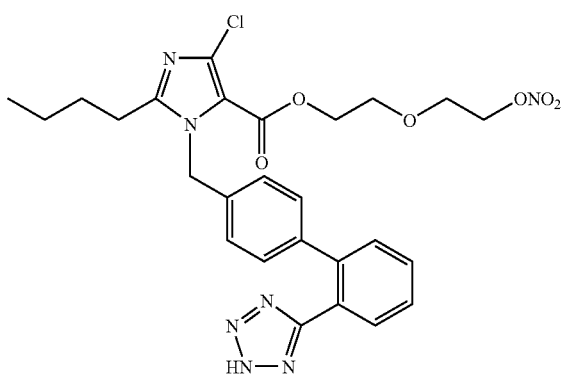 | 1 | 6.0 µM |
| 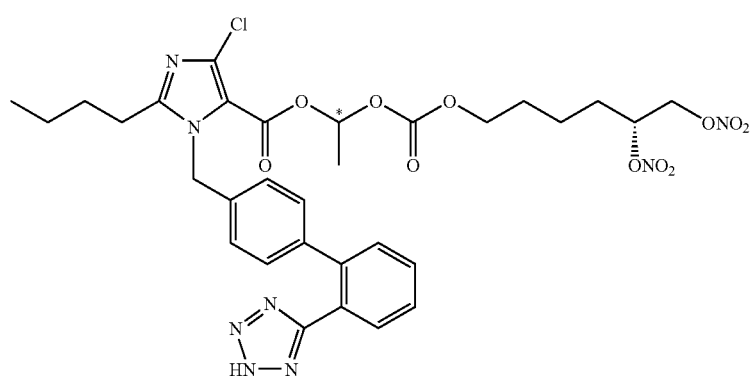 | 2 | 1.0 µM |

DATA TABLE 1-continued

| Structure | Compound Number | EC$_{50}$ in vessel relaxation assay |
|---|---|---|
| (structure shown) | 3 | 1.3 μM |

Compounds 2 and 3 are diastereomers. RNS levels for the tested compounds are shown below in Table 2. CYP inhibition data for tested compounds are shown in Table 3.

NMR

Compound 2:

1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate—Diastereomer A (the second diastereomer to elute by HPLC chromatography on silica gel—see EXAMPLE 1).

$^1$H-NMR (500 MHz, CD$_3$CN): δ 7.71 (d, J=7.5 Hz, 1H), 7.65 (t, J=7.5 Hz, 1H), 7.55 (t, J=7.5 Hz, 1H), 7.51 (d, J=7.5 Hz, 1H), 7.10 (d, J=8.2 Hz, 2H), 6.98 (d, J=8.2 Hz, 2H), 6.80 (q, J=5.5 Hz, 1H), 5.50 (dd, J=27.2, 16.7 Hz, 2H), 5.32 (ddd, J=13.0, 6.5, 2.5 Hz, 1H), 4.79 (dd, J=13.0, 2.5 Hz, 1H), 4.54 (dd, J=13.0, 6.5 Hz, 1H), 4.09 (t, J=6.5 Hz, 2H), 2.60 (t, J=7.7 Hz, 2H), 1.73 (hex, J=7.5 Hz, 2H), 1.64 (p, J=7.5 Hz, 2H), 1.58 (p, J=7.5 Hz, 2H), 1.49 (d, J=5.5 Hz, 3H), 1.44 (hex, J=7.5 Hz, 2H), 1.31 (hex, J=7.5 Hz, 2H), 0.85 (t, J=7.5 Hz, 3H).

Compound 3:

1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate—Diastereomer B (the first diastereomer to elute by HPLC chromatography on silica gel—see EXAMPLE 1).

$^1$H-NMR (500 MHz, CD$_3$CN): δ 7.69 (d, J=7.5 Hz, 1H), 7.62 (t, J=7.5 Hz, 1H), 7.52 (t, J=7.5 Hz, 1H), 7.48 (d, J=7.5 Hz, 1H), 7.07 (d, J=8.0 Hz, 2H), 6.96 (d, J=8.0 Hz, 2H), 6.81 (q, J=5.5 Hz, 1H), 5.50 (dd, J=28.5, 16.5 Hz, 2H), 5.33 (ddd, J=13.0, 6.5, 2.5 Hz, 1H), 4.79 (dd, J=13.0, 2.5 Hz, 1H), 4.55 (dd, J=13.0, 6.5 Hz, 1H), 4.09 (t, J=6.5 Hz, 2H), 2.57 (t, J=7.5 Hz, 2H), 1.74 (hex, J=7.5 Hz, 2H), 1.64 (p, J=7.5 Hz, 2H), 1.55 (p, J=7.5 Hz, 2H), 1.49 (d, J=5.5 Hz, 3H), 1.44 (hex, J=7.5 Hz, 2H), 1.27 (hex, J=7.5 Hz, 2H), 0.82 (t, J=7.5 Hz, 3H).

Assay for Reactive Nitrogen Species (RNS) (DAN Assay)

RNS were detected as S-nitrosothiols (RNSOs) in EDTA-treated rat plasma using an HPLC fluorescent assay based on the method of Kostka and Park (Methods Enzymol. 1999, 301, 227-235). The method is based on the detection of fluorescent 2,3-naphthotriazole (NAT) formed in the reaction between acidified 2,3-diaminonaphthalene (DAN) and the nitrosonium moiety of RSNOs released by HgCl$_2$-mediated breakdown of the S—NO bond. The reaction mixture was chromatographed by reversed phase HPLC, and the fluorescent signal of the resolved NAT peak was quantified.

Plasma (20 μL) was first diluted 1:1 in H$_2$O (20 μL) in a black polypropylene untreated microtiter plate. DAN reagent (100 μL per well, 100 μM DAN in 0.1 N HCl, 4 mM HgCl$_2$) was added, and the plate was immediately sealed with an opaque plate mat, vortexed, and incubated in the dark for 10 min. Plates were centrifuged (2000×g, 5 min) and chilled to 4° C. before HPLC analysis. HPLC was carried out on an Agilent 1200 system using a chilled autosampler (4° C.). Samples were chromatographed on a C8 column (Zorbax Eclipse XDB-C8, 4.6×150 mm, 5 μm) with isocratic elution using a mobile phase of 67% MeOH, 0.1% NH$_4$OAc and a flow rate of 2 mL/min. NAT fluorescence was monitored at 450 nm using an excitation wavelength of 360 nm. Calibration curves were prepared using NaNO$_2$ in control plasma. Typical range of quantitation was 0.1 μM to 30 μM NO$_2$.

Data Table 2
RNS levels - Compounds 1, 2 and 3 and Example 3

| Time(h) | 1 | 2 | 3 | Example 3 |
|---|---|---|---|---|
| 0 | 0.4 ± 0.12 | 1.8 ± 0.13 | 1.4 ± 0.25 | 0.5 |
| 1 | 2.8 ± 0.74 | 5.7 ± 1.32 | 7.4 ± 1.86 | 12.5 |
| 3 | 1.4 ± 0.33 | 5.2 ± 0.49 | 4.4 ± 0.96 | 9.06 |
| 6 | 0.9 ± 0.31 | 3.1 ± 0.86 | 3.0 ± 1.14 | 2.0 |
| 24 | 0.0 ± 0.06 | 1.6 ± 0.36 | 0.6 ± 0.10 | 0.0 |

CYP3A4 Time-Dependent Inhibition Assay

Pooled human liver microsomes (1 mg/mL) were preincubated at 37° C. with 10 and 50 μM of Compound 2 or Compound 3 in 100 mM potassium phosphate buffer (pH 7.4) with 1 mM EDTA, 6 mM MgCl$_2$, and an NADPH-generating system for a duration ranging from 5 to 30 min. The incubation mixtures were diluted 10-fold with the same buffer containing 250 μM testosterone and an NADPH-generating system. The incubation was continued for an additional 10 min to monitor the extent of testosterone 6β-hydroxylation. The first order rate constants ($k_{obs}$) for inactivation at 10 and 50 μM were calculated from the negative slope of the lines by linear regression analysis of the natural logarithm of the remaining activity as a function of time using KaleidaGraph Synergy Software (Reading, Pa.).

Compound 2 caused time-dependent inhibition of CYP3A4 activity at 10 and 50 µM, with a rate constant of 0.026 and 0.037 min$^{-1}$, respectively. In comparison, Compound 3 was a more potent time-dependent inhibitor of CYP3A4, with rate constants ~0.077 min$^{-1}$ at 10 and 50 µM.

Data Table 3
CYP inhibition - Compounds 2 and 3

| Compound | Rate Constant ($k_{obs}$) at 10 µM (min$^{-1}$) | Rate Constant ($k_{obs}$) at 50 µM (min$^{-1}$) |
|---|---|---|
| Compound 2 | 0.026 | 0.037 |
| Compound 3 | 0.077 | 0.076 |
| Mifepristone | 0.077 | 0.070 |

Rate constant of solvent control = 0.006/0.007 min$^{-1}$

The angiotensin II receptor antagonists of the invention are useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system.

The angiotensin II receptor antagonists of the invention are especially useful for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In one embodiment, the invention relates to a method for the treatment and/or prophylaxis of diseases, which are associated with a dysregulation of the renin-angiotensin system, in particular to a method for the treatment or prophylaxis of the above-mentioned diseases, said methods comprising administering to a patient a pharmaceutically active amount of an angiotensin II receptor antagonist of the invention.

The invention also relates to the use of angiotensin II receptor antagonists of the invention for the preparation of a medicament for the treatment and/or prophylaxis of the above-mentioned diseases.

The above-mentioned angiotensin II receptor antagonists of the invention are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren ((2S,4S, 5S,7S)-N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone)) or with other drugs beneficial for the prevention or the treatment of the above-mentioned diseases including nitroprusside and diazoxide.

The dosage regimen utilizing the angiotensin II receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the angiotensin II receptor antagonists, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, and more preferably 25 mg/day to 150 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the angiotensin II receptor antagonists may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The angiotensin II receptor antagonists of the invention can be administered in such oral forms as tablets, capsules and granules. The angiotensin II receptor antagonists are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose aetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

2-Butyl-4-chloro-1-[(2'-(1-H-tetrazol-5-yl)biphenyl-4-yl)methyl]-imidazole-5-carboxylic acid is the active metabolite of 2-butyl-4-chloro-1-[p-(o-1H-tetrazol-5-ylphenyl)-benzyl]imidazole-5-methanol which is available as a monopotassium salt (also known as losartan potassium salt). Losartan potassium salt is available commercially as the active ingredient in COZAAR® (Merck & Co., Inc. (Whitehouse Station, N.J.)). The preparation of losartan potassium salt is described in U.S. Pat. Nos. 5,138,069, 5,130,439, and 5,310,928. Tetrazolylphenylboronic acid intermediates useful in the synthesis of losartan potassium salt are described in U.S. Pat. No. 5,206,374. Additional patents which describe procedures useful for making losartan include U.S. Pat. Nos. 4,820,843, 4,870,186, 4,874,867, 5,039,814, and 5,859,258.

Compounds of the invention can be prepared using losartan potassium salt as the starting material, forming the corresponding carboxylic acid as in Step A, protecting the tetrazole ring as in Step B, preparing a bis-nitrooxy compound that is suitable for linking to the compound formed in Step B, using the bis-nitrooxy compound to form an ester and deprotecting as in Step C, and forming the desired salt (e.g., the potassium salt as in Step D). Alternatively, compounds can be prepared using losartan potassium as the starting material, forming the corresponding carboxylic acid as in Step A, preparing a bis-nitroxy compound that is suitable for linking to the compound formed in Step A, using the bis-nitroxy compound to form a ester, and forming the desired salt (e.g., the potassium salt as in Step D).

Alternatively, compounds can be prepared using 2-Ethoxy-1-[[2'-(1-trityl-1H-tetrazol-5-yl)[1,1'-biphenyl]-4-yl]methyl]-1H-benzimidazole-7-carboxylic acid as the starting material, preparing a bis-nitrooxy compound that is suitable for linking to the starting compound, using the bis-nitroxy compound to form a ester, and forming the desired salt (e.g., the potassium salt as in Step D).

EXAMPLE 1

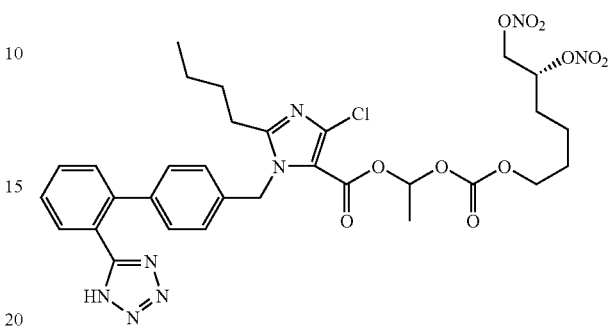

Step A: (2-butyl-4-chloro-1-{[2'-(1H-tetrazol-5-yl)biphenyl-4-yl]methyl}-1H-imidazole-5-carboxylic acid (E3174)

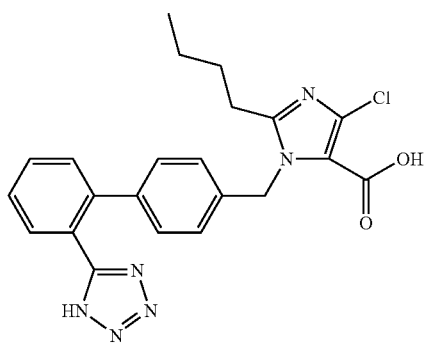

Water (10 L) was added to a 22 L 4-neck round bottom flask. The water was cooled to 0° C. At 0° C., potassium hydroxide (855 g, 15.24 mol) was added followed by losartan potassium (500 g, 1.09 mol)), sodium periodate (554 g, 2.59 mol) and ruthenium(III)chloride hydrate (12 g, 0.05 mol) and the reaction mixture was stirred at 0° C. overnight. The reaction mixture was filtered. IPA (90 mL) was added to the filtrate while stirring. The solution was warmed to 25° C. and stirred for 2.5 hrs. After 2.5 hrs., phosphoric acid (1200 mL) was added, maintaining the temperature below +30° C. The mixture was stirred for 30 min and the product was filtered, washing with water. The residue was dried in the vacuum oven at 55° C. overnight. The solid was dissolved in methanol (4 L) and isopropyl acetate (12 L), and charcoal (activated carbon) (100 g) was added. The mixture was stirred at rt for 3.5 hrs, filtered and concentrated. The product was redissolved in DCM/MeOH and precipitated with heptane to afford the title compound as a greenish/brown foam which was used in subsequent steps without further purification.

Step B: 2-butyl-4-chloro-1-{[2'-(2-trityl-2H-tetrazol-5-yl)biphenyl-4-yl]methyl}-1H-imidazole-5-carboxylic acid

Step C: 1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate

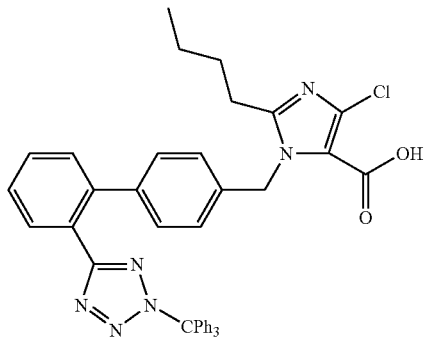

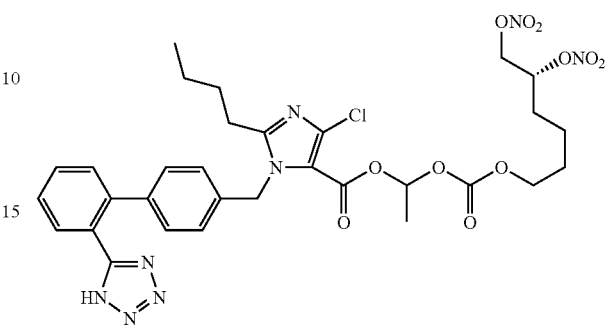

To a solution of E3174 (234.58 g, 0.54 mol) in DCM (4500 mL) was added triethylamine (85 mL, 0.59 mol) followed by a solution of trityl chloride (159 g, 0.56 mol) in DCM (800 mL) and the reaction mixture was stirred at rt overnight. The reaction mixture was washed with water, dried (MgSO4), filtered, and concentrated in vacuo. Chromatography over silica eluting with 20-80% acetone/heptane afforded the title compound as an orange solid.

Preparation of (2R)-6-hydroxyhexane-1,2-diyl dinitrate

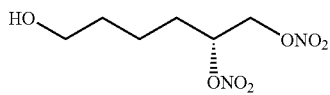

The title compound was prepared as described in WO2005070868(A1).

Preparation of (5R)-5,6-bis(nitrooxy)hexyl 1-chloroethyl carbonate

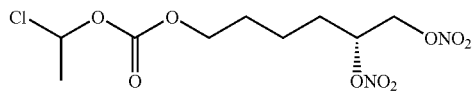

1-Chloroethyl chloroformate (6.42 mL, 58.9 mmol) was added dropwise to a stirred solution of (2R)-6-hydroxyhexane-1,2-diyl dinitrate (12 g, 53.5 mmol) and triethylamine (8.95 mL, 64.2 mmol) in DCM (268 mL) at 0° C. After 2 h, the solution was washed with water, dried (MgSO4), filtered and concentrated in vacuo. The residue was purified by column chromatography on silica gel eluting with 5-40% EtOAc/hexanes to give the title compound as a colorless oil. 1H NMR (500 MHz, CDCl3) δ 6.40 (q, J=6.0 Hz, 1H), 5.28 (ddd, J=13.0, 6.2, 3.0 Hz, 1H), 4.74 (dd, J=13.0, 3.0 Hz, 1H), 4.47 (dd, J=13.0, 6.5 Hz, 1H), 4.25-4.16 (m, 2H), 1.82 (d, J=6.0 Hz, 3H), 1.82-1.71 (m, 4H), 1.63-1.46 (m, 2H).

(5R)-5,6-bis(nitrooxy)hexyl 1-chloroethyl carbonate (7.67 g, 23.2 mmol) was added to a stirred solution of 2-butyl-4-chloro-1-{[2'-(1-trityl-1H-tetrazol-5-yl)biphenyl-4-yl]methyl}-1H-imidazole-5-carboxylic acid (6.30 g, 9.3 mmol) and Cs2CO3 (3.02 g, 9.3 mmol) in DMF (186 mL). The solution was stirred at 70° C. for 2 h. Water (50 mL) was added and the solution was extracted with EtOAc (3×100 mL). The combined organic layers were dried (MgSO4), filtered, and concentrated in vacuo. The residue was redissolved in MeOH (186 mL). After stirring at 70° C. for 2 h, the solution was concentrated in vacuo. The residue was purified by HPLC chromatography (50×100 mm C-18) eluting with 40-100% MeCN/water+0.05% TFA. The diastereomers were then separated by HPLC chromatography on silica gel (ChiralPak AD-H) eluting with 20% MeOH in supercritical CO2 to give the title compound as a white solid. 1H NMR (500 MHz, CD3OD) δ 8.06 (d, J=7.5 Hz, 1H), 7.62 (td, J=7.5, 1.0 Hz, 1H), 7.56 (td, J=6.5, 1.0 Hz, 1H), 7.44 (d, J=6.5 Hz, 1H), 7.17 (d, J=8.0 Hz, 2H), 6.99 (d, J=8.0 Hz, 2H), 6.87 (q, J=5.5 Hz, 1H), 5.54 (d, J=6.0 Hz, 2H), 5.24 (ddd, J=13.0, 6.2, 3.0 Hz, 1H), 4.73 (dq, J=12.5, 1.5 Hz, 1H), 4.46 (dd, J=13.0, 6.5 Hz, 1H), 4.14-4.04 (m, 1H), 2.76 (t, J=7.7 Hz, 2H), 1.76-1.59 (m, 6H), 1.61 (d, J=5.5 Hz, 3H) 1.55-1.40 (m, 2H), 1.38 (hex, J=7.5 Hz, 2H), 0.90 (t, J=7.5 Hz, 3H); LCMS (M+H) found 731.1.

The two diastereomers were separated and evaluated as Diastereomers A and B

Step D: Potassium 5-(4'-{[5-({1-[({[(5R)-5,6-bis(nitrooxy)hexyl]oxy}carbonyl)oxy]ethoxy}-carbonyl)-2-butyl-4-chloro-1H-imidazol-1-yl]methyl}biphenyl-2-yl)tetrazol-1-ide

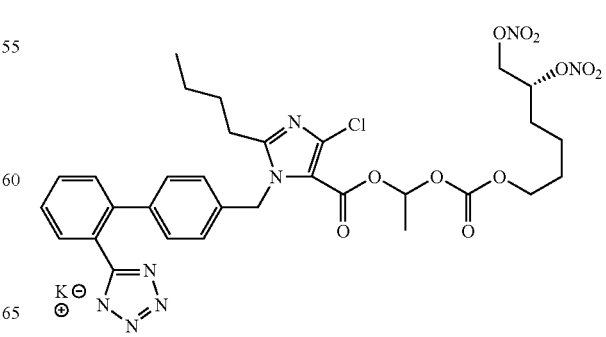

Potassium carbonate (945 mg, 6.84 mmol) was added to a stirred solution of 1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate (250 mg, 0.34 mmol) in IPA (6.8 mL). The solution was stirred at 25° C. for 3 h. The reaction mixture was filtered and the filtrate was concentrated in vacuo. The residue was redissolved in DCM (6 mL). Heptane was added until the compound began to precipitate. The solution was concentrated in vacuo to give the title compound as a white solid. 1H NMR (500 MHz, CD3CN) δ 7.72-7.68 (m, 1H), 7.40-7.33 (m, 2H), 7.33-7.28 (m, 1H), 7.12 (d, J=8.5 Hz, 2H), 6.87 (d, J=8.0 Hz, 2H), 6.88-6.82 (m, 1H), 5.47 (s, 2H), 5.32 (ddd, J=13.0, 6.5, 2.5 Hz, 1H), 4.79 (dd, J=13.0, 2.5 Hz, 1H), 4.55 (dd, J=13.0, 6.5 Hz, 1H), 4.08 (td, J=6.5, 3.0 Hz, 2H), 1.71 (q, J=13.0, 7.7 Hz, 2H), 1.61 (hex, J=22.0, 14.5, 7.0 Hz, 4H), 1.50 (d, J=5.5 Hz, 3H) 1.49-1.37 (m, 2H), 1.35-1.26 (m, 2H), 0.85 (t, J=7.5 Hz, 3H); LCMS (M+H) found 731.1.

1-[({[(5R)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate formed in Step C was also separated into two diastereomers using HPLC chromatography on silica gel (ChiralPak AD-H) column using 25% MeOH in supercritical $CO_2$ (4.6×250 mm, 20% MeOH/80% $CO_2$, 2.1 nml/min, 100 bar, 40° C.) with diastereomer A the second in time to elute and diastereomer B the first in time to elute:

|  | Time | Area |
| --- | --- | --- |
| Diastereomer B | 7.80 min | 142.9 mV.Min (47.526%) |
| Diastereomer A | 9.52 min | 155.0 mV.Min (51.568%) |

Intermediate 1

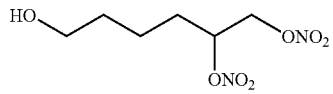

6-hydroxyhexane-1,2-diyl dinitrate

Step A: 5,6-bis(nitrooxy)hexyl 4-nitrobenzoate

To an acetonitrile (100 mL) solution of hex-5-en-1-yl 4-nitrobenzoate (prepared as described in WO2005070868(A1)) (5.00 g, 20.06 mmol) at −20° C. was added silver nitrate (4.09 g, 24.07 mmol) and iodine (6.11 g, 24.07 mmol). The mixture was stirred at −20° C. for 10 minutes. Silver nitrate was added (8.52 g, 50.15 mmol), and the mixture was heated in a microwave apparatus (40 minutes, 120° C.). The silver salts were filtered off, and the solution was concentrated. The residue was purified by flash chromatography (Biotage SP1, 65i column, TLC method n-hexane/ethyl acetate 7/3, $R_f$: 0.30), affording the title compound.

Step B: 6-hydroxyhexane-1,2-diyl dinitrate

To a tetrahydrofuran/ethanol 1:1 (12 mL) solution of 5,6-bis(nitrooxy)hexyl 4-nitrobenzoate (2.5 g, 6.70 mmol) at 0° C. was added 2.5 N sodium hydroxide (6.5 mL) dropwise. The solution was stirred at room temperature for 3 hours. The solution was diluted with a solution of sodium bicarbonate (10 mL) and extracted with ethyl acetate (3×25 mL). The organic layer was washed with brine, dried over sodium sulfate, and concentrated in vacuo, affording the title compound. $^1$H NMR (300 MHz, $CDCl_3$) δ: 5.45-5.38 (m, 1H), 4.94 (dd, 1H), 4.73-4.67 (m, 1H), 4.43 (t, 1H), 3.40-3.36 (m, 2H), 1.75-1.68 (m, 2H), 1.43-1.36 (m, 4H).

Intermediate 2

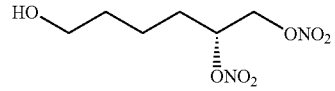

(2R)-6-hydroxyhexane-1,2-diyl dinitrate

The title compound was prepared as described in WO2005070868(A1).

Intermediate 3

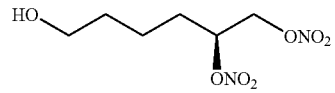

(2S)-6-hydroxyhexane-1,2-diyl dinitrate

The title compound was prepared as described in WO2005070868(A1).

Intermediate 4

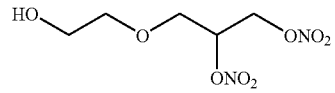

3-(2-hydroxyethoxy)propane-1,2-diyl dinitrate

The title compound was prepared by following the procedure for intermediate 1, except that the reagent hex-5-en-1-yl 4-nitrobenzoate was replaced by 2-allyloxyethyl 4-nitrobenzoate. $^1$H NMR (300 MHz, $CDCl_3$) δ: 5.50-5.38 (m, 1H), 4.85 (dd, 1H), 4.68 (dd, 1H), 3.85-3.72 (m, 4H), 3.70-3.58 (m, 2H).

Intermediate 5

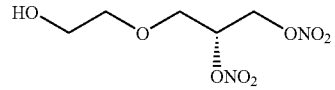

(2R)-3-(2-hydroxyethoxy)propane-1,2-diyl dinitrate

The title compound was prepared by following the procedure for examples 4 and 6 in WO2005070868(A1), except that the reagent hex-5-en-1-ol was replaced by 2-(allyloxy) ethanol.

Intermediate 6

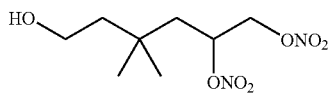

6-hydroxy-4,4-dimethylhexane-1,2-diyl dinitrate

Step A: 2,2-dimethylpent-4-enal

A 2-L round-bottom flask was charged with p-cymene (800 mL), allylic alcohol (290 mL, 4.27 mol), isobutylaldehyde (588 mL, 6.40 mol), and p-toluenesulfonic acid (2 g). The flask was fitted with a Dean-Stark apparatus, and the mixture was refluxed for 36 hours to remove water azeotropically. The Dean-Stark apparatus was removed and replaced by a Rashig-ring packed column. The mixture was distilled to collect the fraction at 93-135° C. The distilled fraction was washed with water to remove allyl alcohol, dried over sodium sulfate, filtered and redistilled. The fractions distilled before 180° C. were discarded, and distillate at 180-205° C. was collected to give the title compound as a yellow oil.

Step B: 1-methoxy-3,3-dimethylhexa-1,5-diene

To a freshly prepared tetrahydrofuran (300 mL) solution of lithium diisopropylamide (0.19 mol) under nitrogen at 0° C. was added dropwise in 30 minutes a tetrahydrofuran (200 mL) solution of diphenyl(methoxymethyl)phosphinoxide (49.5 g, 0.2 mol). After stirring for 15 minutes at 0° C., a tetrahydrofuran (100 mL) solution of 2,2-dimethylpent-4-enal (24.5 g, 0.22 mol) was added dropwise in 20 minutes to the cherry-colored mixture. After 15 minutes, the mixture was warmed to room temperature and then refluxed for 5 hours. The mixture was cooled to room temperature, charged with water (20 mL), and cooled at 0° C. under vigorous stirring. The resulting solid was filtered, washed with hexanes, and discarded. The filtrates were collected and distilled at 101-102° C. (155 mmHg) to give the title compound as a colorless oil.

Step C: 3,3-dimethylhex-5-enal

In a 500-mL round-bottom flask, sulfuric acid (48 mL; 30%) was added to a stirred tetrahydrofuran (150 mL) solution of 1-methoxy-3,3-dimethylhexa-1,5-diene (15.89 g, 0.113 mol). After the mixture had been stirred for 1 hour, it was gradually poured into saturated sodium bicarbonate (ca. 500 mL), and then extracted with diethyl ether (4×200 mL). The combined extracts were washed with brine, dried over sodium sulfate, and filtered. Evaporation of the solvent gave the title compound as a pale yellow liquid.

Step D: 3,3-dimethylhex-5-en-1-ol

In a 1-L 4-necked round-bottom flask, 3,3-dimethylhex-5-enal (14.20 g; 0.113 mol) was dissolved in absolute ethanol (420 mL). Then the mixture was cooled to 5° C. in an ice-bath and, under nitrogen atmosphere, sodium borohydride (3.3 g; 0.087 mol) was added cautiously in 10 minutes. After the mixture had been stirred for 1 hour, it was poured into 5% ammonium chloride, diluted with water, and extracted with dichloromethane. Extracts were dried over sodium sulfate and evaporated, then the white solid was filtered away, while the pale yellow oil was distilled at 55-56° C. (4 mmHg) to give the title compound as a foul smelling, colorless liquid.

Step E: 3,3-dimethylhex-5-enyl 4-nitrobenzoate

In a 500-mL, two-necked round-bottom flask, 3,3-dimethylhex-5-en-1-ol (5.30 g, 0.041 mol) and triethylamine (16 mL, 0.057 mol) were dissolved in dichloromethane (110 mL), and then the mixture was cooled, under nitrogen atmosphere, in an ice bath to 5° C. A dichloromethane (10 mL) solution of 4-nitrobenzoyl chloride (9.1 g, 0.049 mol) was added dropwise in 20 minutes. After the mixture had been stirred at 5-10° C. for 1 hour, water was added. The organic layer was washed with acid, water, brine, dried over sodium sulfate, and filtered. After evaporation of the solvent, the crude product was purified by column chromatography (silica gel; ethyl acetate/hexanes 1/9 as eluant) to give the title compound as a yellow liquid.

Step F: 6-hydroxy-4,4-dimethylhexane-1,2-diyl dinitrate

The title compound was prepared by following the procedure for intermediate 1, except that the reagent hex-5-en-1-yl 4-nitrobenzoate was replaced by 3,3-dimethylhex-5-enyl 4-nitrobenzoate.

Intermediate 7

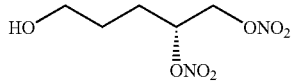

(2R)-5-hydroxypentane-1,2-diyl dinitrate

Step A: ethyl 3-[(4R)-2,2-dimethyl-1,3-dioxolan-4-yl]propanoate

To a methanol (200 mL) solution of ethyl (2E)-3-[(4R)-2,2-dimethyl-1,3-dioxolan-4-yl]acrylate (15.3 g, 76.7 mmol) was added 10% palladium on carbon (1.5 g). The reaction mixture was stirred under an atmosphere of hydrogen overnight. The catalyst was removed by filtration, and the solvent was removed in vacuo. Chromatography over silica afforded the title compound. $^1$H NMR (400 MHz, CDCl$_3$): δ 4.05-4.15 (m, 2H), 4.02-4.04 (m, 2H), 3.52-3.55 (m, 1H), 2.30-2.47 (m, 2H), 1.83-1.90 (m, 2H), 1.33 (s, 3H), 1.26 (s, 3H), 1.21 (t, J=6.8 Hz, 3H).

Step B: 3-[(4R)-2,2-dimethyl-1,3-dioxolan-4-yl]propan-1-ol

To a suspension of lithium aluminium hydride (1.40 g, 35.6 mmol) in anhydrous tetrahydrofuran (100 mL) was added dropwise a tetrahydrofuran solution (30 mL) of ethyl 3-[(4R)-2,2-dimethyl-1,3-dioxolan-4-yl]propanoate (6.00 g, 29.7 mmol) at 0° C. under nitrogen. The reaction mixture was stirred at room temperature overnight, then quenched with the addition of water (1.4 mL) and 10% aqueous sodium hydroxide (1.4 mL). The white solid was removed by filtration, and the filtrate was concentrated in vacuo. The residue was partitioned between water (50 mL) and ethyl acetate (50 mL). The organic phase was washed with brine, dried (sodium sulfate), and concentrated in vacuo to afford the title compound. $^1$H NMR (300 MHz, CDCl$_3$): δ 4.03-4.13 (m, 2H), 3.65-3.69 (m, 2H), 3.50-3.55 (m, 1H), 1.61-1.69 (m, 4H), 1.32 (s, 3H), 1.24 (s, 3H).

Step C: 3-[(4R)-2,2-dimethyl-1,3-dioxolan-4-yl]propyl 4-nitrobenzoate

The title compound was prepared by following step E of the synthesis of intermediate 6, except that the reagent 3,3-dimethylhex-5-en-1-ol was replaced by 3-[(4R)-2,2-dimethyl-1,3-dioxolan-4-yl]propan-1-ol. $^1$H NMR (400 MHz, CDCl$_3$): δ 8.30 (d, J=8.4 Hz, 2H), 8.21 (d, J=8.4 Hz, 2H), 4.40-4.43 (m, 2H), 4.05-4.17 (m, 2H), 3.54-3.57 (m, 1H), 1.82-1.95 (m, 2H), 1.62-1.82 (m, 2H), 1.41 (s, 3H), 1.35 (s, 3H).

Step D: (4R)-4,5-bis(nitrooxy)pentyl 4-nitrobenzoate

To a chloroform solution (25 mL) of nitric acid (3.30 mL, 51.7 mmol) at 0° C. was added 3-[(4R)-2,2-dimethyl-1,3-dioxolan-4-yl]propyl 4-nitrobenzoate (1.60 g, 5.17 mmol). After 1 hour, the reaction was quenched by adding it slowly to an ice mixture with sodium bicarbonate. It was extracted with ethyl acetate, and the combined organic extracts were washed with brine, dried (magnesium sulfate), filtered, and concentrated in vacuo. The crude product was carried out to the next step without further purification. $^1$H NMR (500 MHz, CD$_3$CN) δ 8.30 (d, J=8.9 Hz, 2H), 8.20 (d, J=8.9 Hz, 2H), 5.48-5.56 (m, 1H), 4.84 (dd, J=3.2, 13.0 Hz, 1H), 4.71 (dd, J=6.8, 13.0 Hz, 1H), 4.48 (t, J=4.5 Hz, 2H), 3.80-3.92 (m, 4H).

Step E: (2R)-5-hydroxypentane-1,2-diyl dinitrate

The title compound was prepared by following the procedure for example 6 in WO2005070868(A 1), except that the reagent (5R)-5,6-bis(nitrooxy)hexyl 4-nitrobenzoate was replaced by (4R)-4,5-bis(nitrooxy)pentyl 4-nitrobenzoate. $^1$H NMR (500 MHz, CD$_3$CN) δ 5.42 (dq, J=2.6, 6.6 Hz, 1H), 4.84 (dd, J=2.6, 12.9 Hz, 1H), 4.48 (dd, J=6.2, 13.0 Hz, 1H), 3.54 (t, J=6.3 Hz, 2H), 1.82 (q, J=7.4 Hz, 2H), 1.54-1.68 (m, 2H).

Intermediate 8

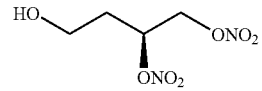

(2S)-4-hydroxybutane-1,2-diyl dinitrate

Step A: [(4S)-2,2-dimethyl-1,3-dioxolane-2-ethyl]-4-nitrobenzoate

The title compound was prepared by following step E of the synthesis of intermediate 6, except that the reagent 3,3-dimethylhex-5-en-1-ol was replaced by (4S)-4-(2-hydroxyethyl)-2,2-dimethyl-1,3-dioxolane. $^1$H NMR (300 MHz, CDCl$_3$) δ 8.31 (d, J=8.9 Hz, 2H), 8.22 (d, J=8.9 Hz, 2H), 4.52 (m, 2H), 4.29 (q, J=6.2 Hz, 1H), 4.14 (dd, J=6.0, 8.0 Hz, 1H), 3.66 (dd, J=7.0, 8.0 Hz, 1H), 2.07 (m, 2H), 1.44 (s, 3H), 1.38 (s, 3H).

Step B: (3S)-3,4-dihydroxybutanyl 4-nitrobenzoate

An aqueous solution of acetic acid (70 mL, 70% v/v) containing [(4S)-2,2-dimethyl-1,3-dioxolane-2-ethyl]-4-nitrobenzoate (4.40 g, 15.1 mmol) was heated at 60° C. for 3 hours. The reaction was then cooled to room temperature. Ethyl acetate (100 mL) was added, and the solution was carefully basified using sodium bicarbonate. The organic layer was separated, and the aqueous layer was extracted twice with ethyl acetate (100 mL). The combined organic layers were washed with water and brine, dried over sodium sulfate, filtered, and evaporated. The crude alcohol was recrystallized from diethyl ether/n-hexane to give a white solid. $^1$H NMR (300 MHz, CDCl$_3$) δ 8.31 (d, J=8.9 Hz, 2H), 8.21 (d, J=8.9 Hz, 2H), 4.65 (ddd, J=5.7, 8.4, 11.2 Hz, 1H), 4.52 (dt, J=5.7, 11.2 Hz, 1H), 3.92 (tt, J=3.5, 7.4 Hz, 1H), 3.74 (dd, J=3.5, 11.1 Hz, 1H), 3.56 (dd, J=7.4, 11.1 Hz, 1H), 2.36 (bs, 2H), 1.94 (m, 2H).

Step C: (3S)-3,4-bis(nitrooxy)butanyl 4-nitrobenzoate

At −78° C., to a stirred dichloromethane (30 mL) solution of fuming nitric acid (6.4 mL) was added concentrated sulfuric acid (1.6 mL). After 5 minutes, a dichloromethane/ethyl acetate (4/6, 20 mL) solution of (3S)-3,4-dihydroxybutanyl 4-nitrobenzoate (1.8 g, 7.1 mmol) was added dropwise. The reaction was left for 2 hours at 0° C. before being poured onto ice (300 g). Water was then added, and the organic layer separated, washed with water, brine, dried on sodium sulfate, filtered and concentrated. The residue was purified by column chromatography on silica (20% to 40% ethyl acetate in n-hexane) to give the title compound as an oil. $^1$H NMR (300 MHz, CDCl$_3$) δ 8.34 (d, J=8.8 Hz, 2H), 8.21 (d, J=8.8 Hz, 2H), 5.53 (qd, J=3.3, 6.5 Hz, 1H), 4.86 (dd, J=3.3, 12.9 Hz, 1H), 4.57 (m, 3H), 2.29 (dd, J=6.2, 12.3 Hz, 2H).

Step D: (2S)-4-hydroxybutane-1,2-diyl dinitrate

The title compound was prepared by following step B of the synthesis of intermediate 1, except that the reagent 5,6-bis(nitrooxy)hexyl 4-nitrobenzoate was replaced by (3S)-3,4-bis(nitrooxy)butanyl 4-nitrobenzoate. $^1$H NMR (300 MHz, CDCl$_3$) δ 5.56 (ddd, J=2.8, 6.4, 13.0 Hz, 1H), 4.89 (dd, J=2.8, 13.0 Hz, 1H), 4.56 (dd, J=6.4, 13.0 Hz, 1H), 3.84 (td, J=2.7, 5.7 Hz, 2H), 2.02 (dd, J=5.7, 6.4 Hz, 2H), 1.73 (bs, 1H).

Intermediate 9

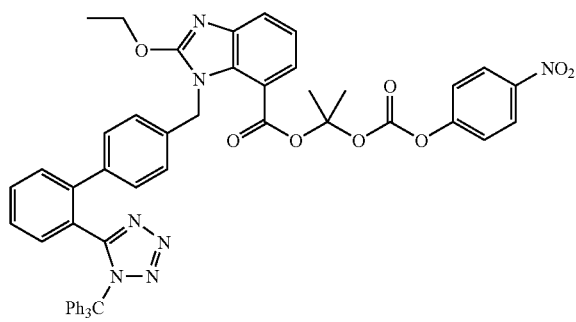

1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate An orange suspension of mercuric oxide (1.17 g, 5.39 mmol) and 2-ethoxy-1-{[2'-(1-trityl-1H-tetrazol-5-yl)biphenyl-4-yl]methyl}-1H-benzimidazole-7-carboxylic acid (7.36 g, 10.8 mmol) in dry tetrahydrofuran (95 mL) was stirred at room temperature for 24 hours. Then 2-chloroisopropyl p-nitrophenyl carbonate (prepared as described in U.S. Pat. No. 5,684,018) (1.40 g, 5.39 mmol) was added, and the reaction was stirred at room temperature for about 7 days and monitored by TLC (hexane/ethyl acetate 6/4). The mixture was diluted with dichloromethane, washed with water, and the organic layer was dried over sodium sulfate and concentrated under reduced pressure. The residue was purified by flash chromatography (Biotage SP1; column 65i; TLC method: n-hexane/ethyl acetate 7/3; $R_f$=0.20), affording the title product.

EXAMPLE 2

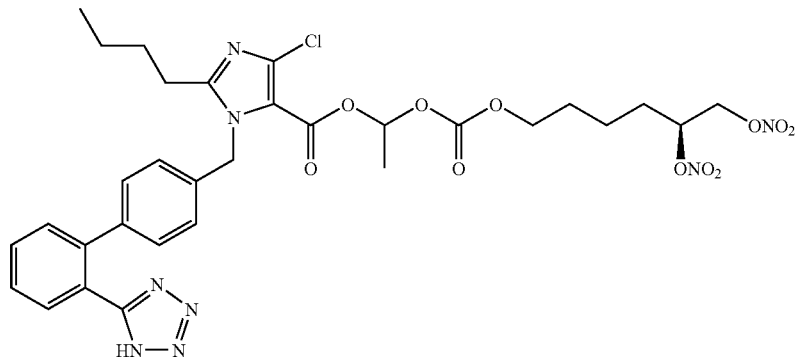

1-[({[(5S)-5,6-bis(nitrooxy)hexyl]oxy}carbonyl)oxy]ethyl 2-butyl-4-chloro-1-{[2'-(1H-tetrazol-5-yl)biphenyl-4-yl]methyl}-1H-imidazole-5-carboxylate The title compound was prepared by following the procedure for example 1, except that the reagent (2R)-6-hydroxyhexane-1,2-diyl dinitrate was replaced by (2S)-6-hydroxyhexane-1,2-diyl dinitrate (intermediate 3).

EXAMPLE 3

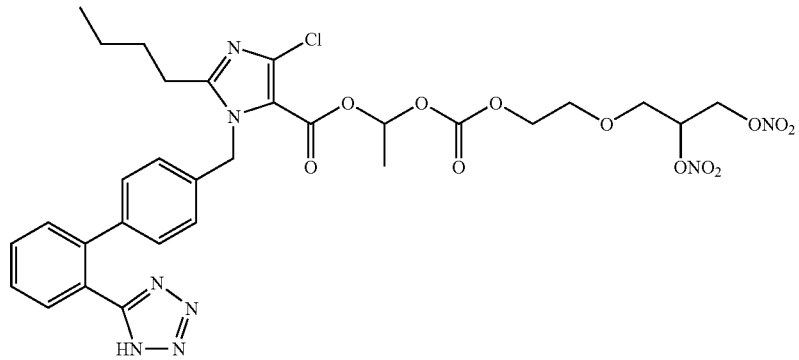

1-[({2-[2,3-bis(nitrooxy)propoxy]ethoxy}carbonyl) oxy]ethyl 2-butyl-4-chloro-1-{[2'-(1H-tetrazol-5-yl) biphenyl-4-yl]methyl}-1H-imidazole-5-carboxylate The title compound was prepared by following the procedure for example 1, except that the reagent (2R)-6-hydroxyhexane-1,2-diyl dinitrate was replaced by 3-(2-hydroxyethoxy)propane-1,2-diyl dinitrate (intermediate 4). $^1$H NMR (300 MHz, CDCl$_3$) δ 8.10 (d, 1H), 7.60 (m, 2H), 7.45 (d, 1H), 7.20 (d, 2H), 7.01 (d, 2H), 6.95 (dd, 1H), 5.54 (s, 2H), 5.35 (m, 1H), 4.80 (dd, 1H), 4.61 (dd, 1H), 4.26 (t, 2H), 3.77-3.65 (m, 4H), 2.69 (t, 2H), 1.80-1.66 (m, 2H) 1.63 (d, 3H), 1.47-1.32 (m, 2H), 0.92 (t, 3H).

EXAMPLE 4

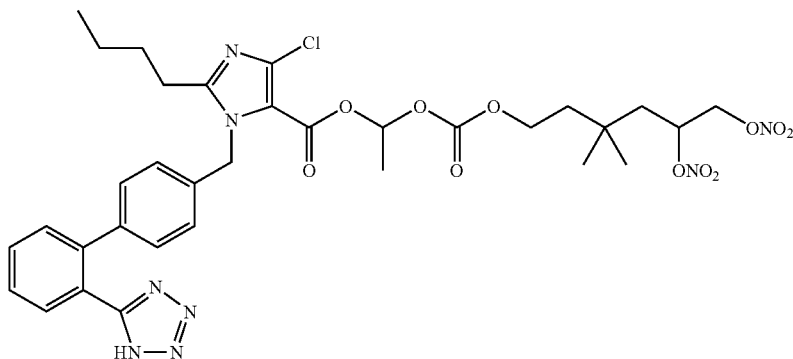

1-[({[3,3-dimethyl-5,6-bis(nitrooxy)hexyl] oxy}carbonyl)oxy]ethyl 2-butyl-4-chloro-1-{[2'-(1H-tetrazol-5-yl)biphenyl-4-yl]methyl}-1H-imidazole-5-carboxylate The title compound was prepared by following the procedure for example 1, except that the reagent (2R)-6-hydroxyhexane-1,2-diyl dinitrate was replaced by 6-hydroxy-4,4-dimethylhexane-1,2-diyl dinitrate (intermediate 6). $^1$H NMR (300 MHz, CDCl$_3$) δ 8.10 (d, 1H), 7.61-7.57 (m, 2H), 7.45 (dd, 1H), 7.19 (d, 2H), 7.00 (d, 2H), 6.87 (q, 1H), 6.87 (q, 1H), 5.53 (s, 2H), 5.47-5.37 (m, 1H), 4.73 (dq, 1H), 4.40 (dd, 1H), 4.19-4.12 (m, 2H), 2.66 (t, 2H), 1.73-1.27 (m, 11H), 1.05-0.76 (m, 9H).

EXAMPLE 5

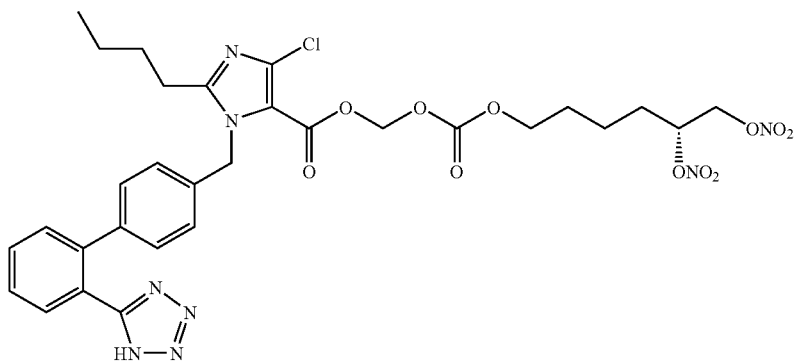

[({[(5R)-5,6-bis(nitrooxy)hexyl]oxy}carbonyl)oxy]methyl 2-butyl-4-chloro-1-{[2'-(1H-tetrazol-5-yl)biphenyl-4-yl]methyl}-1H-imidazole-5-carboxylate The title compound was prepared by following the procedure for example 1, except that the reagent 1-chloroethyl chloroformate was replaced by chloromethyl chloroformate. $^1$H NMR (500 MHz, CDCl$_3$) δ 7.91 (d, J=7.6 Hz, 1H), 7.59 (dt, J=1.2, 7.6 Hz, 1H), 7.51 (dt, J=1.1, 7.7 Hz), 7.42 (d, J=7.6 Hz, 1H), 7.10 (d, J=8.3 Hz, 2H), 6.91 (d, J=8.0 Hz, 2H), 5.85 (s, 2H), 5.48 (s, 2H), 5.25 (dq, J=2.9, 6.6 Hz, 1H), 4.73 (dd, J=3.0, 12.8 Hz, 1H), 4.45 (dd, J=6.5, 12.9 Hz, 1H), 4.13 (t, J=6.3 Hz, 2H), 2.58 (t, J=7.8 Hz, 2H), 1.40-1.80 (m, 6H), 1.61 (quintet, J=7.7 Hz, 2H), 1.36 (sextet, J=7.5 Hz, 2H), 0.84 (t, J=7.4 Hz, 3H); LC-MS: m/z 717 (M+H).

EXAMPLE 6 chloroformate was replaced by 1-chloro-2-methylpropyl chloroformate. $^1$H NMR (500 MHz, CDCl$_3$) δ 7.97-7.91 (m, 1H), 7.60 (t, J=7.5 Hz, 1H), 7.52 (t, J=7.5 Hz, 1H), 7.42 (d, J=7.5 Hz, 1H), 7.11 (d, J=7.5 Hz, 2H), 6.92 (d, J=7.5 Hz, 2H), 6.60 (d, J=4.5 Hz, 2H), 5.54-5.46 (m, 2H), 5.28-5.21 (m, 1H), 4.76-4.70 (m, 2H), 4.45 (dd, J=13.0, 6.5 Hz, 1H), 4.24-4.13 (m, 1H), 4.13-4.03 (m, 1H), 2.70-2.60 (m, 2H), 2.21-2.08 (m, 1H), 1.77-1.68 (m, 2H), 1.68-1.58 (m, 2H), 1.58-1.39 (m, 2H), 1.39-1.29 (m, 2H), 1.02 (d, J=7.0 Hz, 6H), 0.87 (t, J=7.5 Hz, 3H); LC-MS: m/z 759 (M+H).

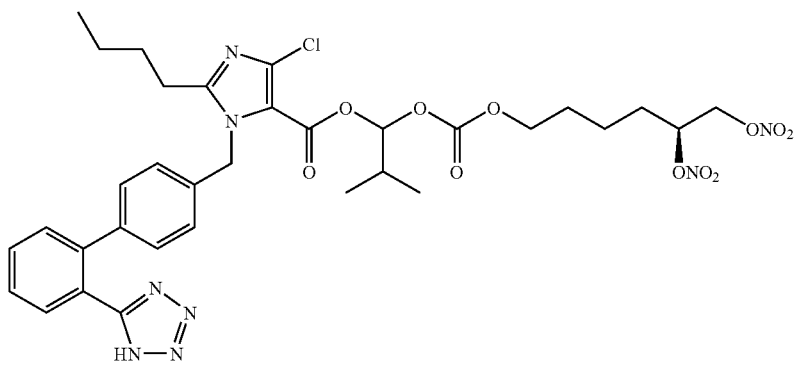

EXAMPLE 7

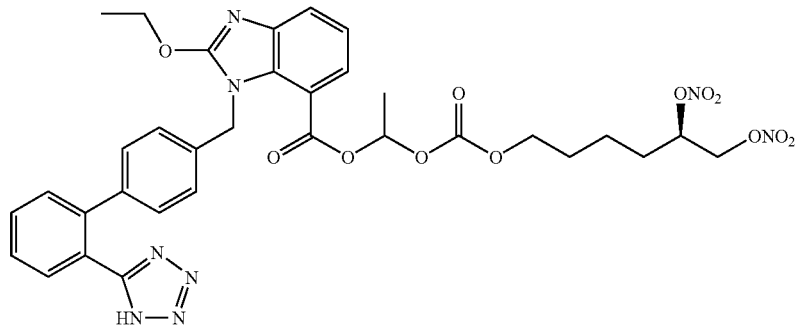

1-[({[(5S)-5,6-bis(nitrooxy)hexyl]oxy}carbonyl)oxy]-2-methylpropyl 2-butyl-4-chloro-1-{[2'-(1H-tetrazol-5-yl)biphenyl-4-yl]methyl}-1H-imidazole-5-carboxylate The title compound was prepared by following the procedure for example 2, except that the reagent 1-chloroethyl 1-[({[(5R)-5,6-bis(nitrooxy)hexyl]oxy}carbonyl)oxy]ethyl 2-ethoxy-1-{[2'-(1H-tetrazol-5-yl)biphenyl-4-yl]methyl}-1H-benzimidazole-7-carboxylate The title compound was prepared by following the procedure for example 1, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H- benzimidazole-7-carboxylic acid. $^1$H NMR (500 MHz, CD$_3$CN) δ 7.71 (d, J=8.0 Hz, 1H), 7.70 (d, J=7.5 Hz, 1H), 7.64 (t, J=7.6 Hz, 1H), 7.62 (d, J=7.5 Hz, 1H), 7.54 (t, J=7.6 Hz, 1H), 7.45 (d, J=7.8 Hz, 1H), 7.27 (t, J=7.9 Hz, 1H), 7.02 (d, J=8.3 Hz, 2H), 6.97 (d, J=8.0 Hz, 2H), 6.80 (q, J=5.4 Hz, 1H), 5.62 (d, J=16.5 Hz, 1H), 5.57 (d, J=16.5 Hz, 1H), 4.78 (dd, J=2.8, 13.1 Hz, 1H), 4.64 (q, J=7.1 Hz, 2H, D1), 4.64 (q, J=7.0 Hz, 2H, D2), 4.53 (dd, J=6.1, 12.9 Hz, 1H), 4.11 (t, J=6.5 Hz, 2H, D1), 4.11 (t, J=6.4 Hz, 2H, D2), 1.72 (q, J=7.6 Hz, 2H), 1.63 (quintet, J=7.0 Hz, 2H), 1.38-1.50 (m, 8H); LC-MS: m/z 735 (M+H).

EXAMPLE 8

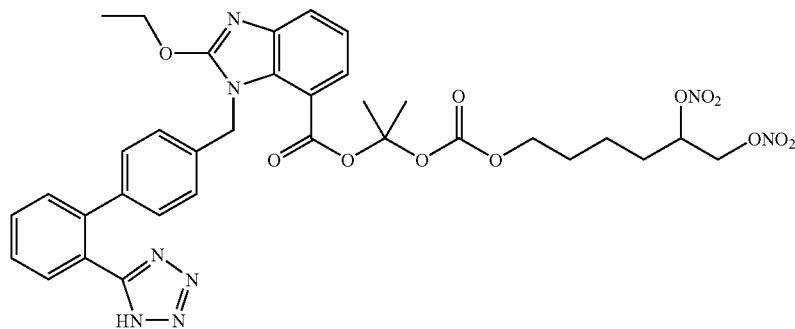

1-[({[5,6-bis(nitrooxy)hexyl]oxy}carbonyl)oxy]-1-methylethyl 2-ethoxy-1-{[2'-(1H-tetrazol-5-yl)biphenyl-4-yl]methyl}-1H-benzimidazole-7-carboxylate Step A: 1-[({[5,6-bis(nitrooxy)hexyl]oxy}carbonyl)oxy]-1-methylethyl 2-ethoxy-1-{[2'-(1-trityl-1H-tetrazol-5-yl)biphenyl-4-yl]methyl}-1H-benzimidazole-7-carboxylate 6-Hydroxyhexane-1,2-diyl dinitrate (intermediate 1, 0.082 g, 0.36 mmol) and N,N-dimethylaminopyridine (0.029 g, 0.11 mmol) were added to a stirred dichloromethane (3.5 mL) solution of 1-methyl-1-{[(4-nitrophenoxy)carbonyl]oxy}ethyl 2-ethoxy-1-{[2'-(1-trityl-1H-tetrazol-5-yl)biphenyl-4-yl]methyl}-1H-benzimidazole-7-carboxylate (intermediate 9, 0.220 g, 0.24 mmol). The solution was stirred at room temperature for 18 hours. Then it was washed with a 5% solution of sodium dihydrogenphosphate (2×10 mL) and brine (10 mL). The organic layer was dried over sodium sulfate, concentrated and purified by flash chromatography (Biotage SP1, 25+M column, TLC method n-hexane/EtOAc 6/4, R$_f$ 0.4), affording the title compound as a white solid. $^1$H NMR (300 MHz, CDCl$_3$) δ 8.04-8.01 (m, 1H), 7.63-7.61 (m, 2H), 7.46-7.18 (m, 12H), 6.98-6.90 (m, 8H), 6.91 (t, 1H), 6.81 (d, 3H), 6.68 (d, 2H), 5.62 (s, 2H), 5.25-5.23 (m, 1H), 4.72 (dd, 1H), 4.28-4.26 (m, 2H), 4.05 (t, 2H), 1.78-1.52 (m, 10H), 1.49-1.42 (m, 6H).

Step B: 1-[({[5,6-bis(nitrooxy)hexyl]oxy}carbonyl)oxy]-1-methylethyl 2-ethoxy-1-{[2'-(1H-tetrazol-5-yl)biphenyl-4-yl]methyl}-1H-benzimidazole-7-carboxylate A dichloromethane/methanol (3.5 mL, 1:7) solution of 1-[({[5,6-bis(nitrooxy)hexyl]oxy}carbonyl)oxy]-1-methylethyl 2-ethoxy-1-{[2'-(1-trityl-1H-tetrazol-5-yl)biphenyl-4-yl]methyl}-1H-benzimidazole-7-carboxylate (0.190 g, 0.192 mmol) was heated in a microwave apparatus (90° C., 20 minutes). Then the solution was concentrated and the residue was purified by flash chromatography (Biotage SP1, 25+M column, dichloromethane/methanol 98/2), affording the title compound. $^1$H NMR (300 MHz, CDCl$_3$) δ 8.04-8.01 (m, 1H), 7.63-7.61 (m, 2H), 7.52 (dd, 1H), 7.32-7.28 (m, 1H), 6.91 (t, 1H), 6.81 (d, 3H), 6.68 (d, 2H), 5.62 (s, 2H), 5.25-5.23 (m, 1H), 4.72 (dd, 1H), 4.28-4.26 (m, 2H), 4.05 (t, 2H), 1.78-1.52 (m, 10H), 1.49-1.42 (m, 6H).

EXAMPLE 9

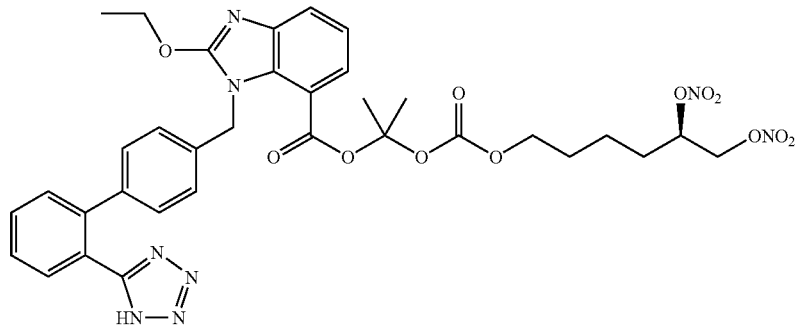

1-[({[(5R)-5,6-bis(nitrooxy)hexyl]oxy}carbonyl)oxy]-1-methylethyl 2-ethoxy-1-{[2'-(1H-tetrazol-5-yl)biphenyl-4-yl]methyl}-1H-benzimidazole-7-carboxylate The title compound was prepared by following the procedure for example 8, except that the reagent 6-hydroxyhexane-1,2-diyl dinitrate was replaced by (2R)-6-hydroxyhexane-1,2-diyl dinitrate (intermediate 2).

EXAMPLE 10

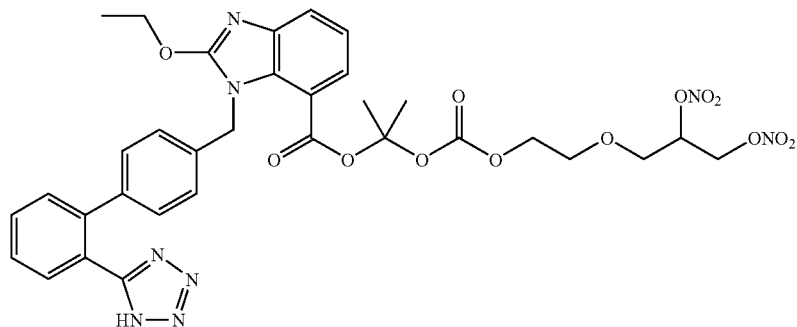

1-[({2-[2,3-bis(nitrooxy)propoxy]ethoxy}carbonyl)oxy]-1-methylethyl 2-ethoxy-1-{[2'-(1H-tetrazol-5-yl)biphenyl-4-yl]methyl}-1H-benzimidazole-7-carboxylate The title compound was prepared by following the procedure for example 8, except that the reagent 6-hydroxyhexane-1,2-diyl dinitrate was replaced by 3-(2-hydroxyethoxy)propane-1,2-diyl dinitrate (intermediate 4). $^1$H NMR (300 MHz, CDCl$_3$) δ: 8.02 (d, 1H), 7.61 (m, 2H), 7.53 (d, 1H), 7.31 (d, 1H), 6.99 (t, 1H), 6.84 (d, 2H), 6.70 (d, 2H), 5.61 (d, 2H), 5.33 (m, 1H), 4.76 (dd, 1H), 4.59 (dd, 1H), 4.40-4.13 (m, 4H), 3.76-3.61 (m, 4H), 1.50 (s, 6H), 1.28 (t, 3H).

EXAMPLE 11

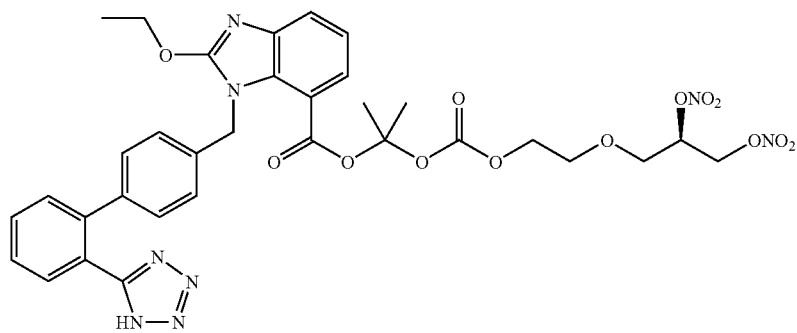

1-{[(2-{[(2R)-2,3-bis(nitrooxy)propyl]oxy}ethoxy) carbonyl]oxy}-1-methylethyl 2-ethoxy-1-{[2'-(1H-tetrazol-5-yl)biphenyl-4-yl]methyl}-1H-benzimidazole-7-carboxylate The title compound was prepared by following the procedure for example 8, except that the reagent 6-hydroxyhexane-1,2-diyl dinitrate was replaced by (2R)-3-(2-hydroxyethoxy)propane-1,2-diyl dinitrate (intermediate 5).

EXAMPLE 12

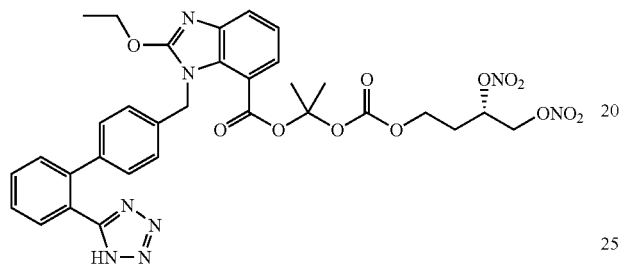

1-[({[(3S)-3,4-bis(nitrooxy)butyl]oxy}carbonyl) oxy]-1-methylethyl 2-ethoxy-1-{[2'-(1H-tetrazol-5-yl)biphenyl-4-yl]methyl}-1H-benzimidazole-7-carboxylate The title compound was prepared by following the procedure for example 8, except that the reagent 6-hydroxyhexane-1,2-diyl dinitrate was replaced by (2S)-4-hydroxybutane-1,2-diyl dinitrate (intermediate 8). $^1$H NMR (300 MHz, CDCl$_3$) δ 8.03 (d, J=6.7 Hz, 1H), 7.63 (m, 2H), 7.52 (d, J=7.7 Hz, 1H), 7.30 (d, J=7.5 Hz, 1H), 6.91 (t, J=7.5 Hz, 2H), 6.82 (d, J=8.0 Hz, 2H), 6.68 (d, J=7.8 Hz, 2H), 5.61 (s, 2H), 5.37 (m, 1H), 4.80 (dd, J=13.0, 3.1 Hz, 1H), 4.50 (dd, J=13.0, 5.9 Hz, 1H), 4.23 (m, 4H), 2.08 (dd, J=12.5, 5.9 Hz, 2H), 1.63 (s, 6H), 1.44 (t, J=7.1 Hz, 3H).

EXAMPLE 13

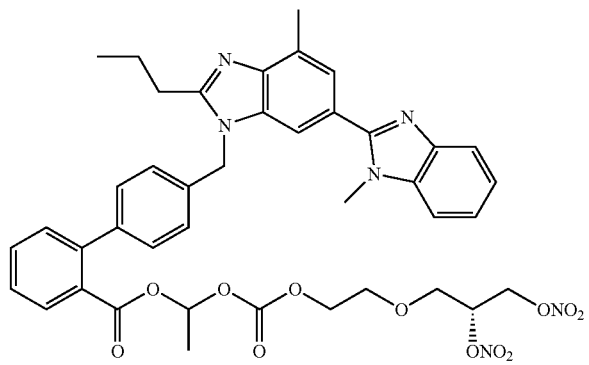

1-{[(2-{[(2R)-2,3-bis(nitrooxy)propyl]oxy}ethoxy) carbonyl]oxy}ethyl 4'-[(1,7'-dimethyl-2'-propyl-1H, 3'H-2,5'-bibenzimidazol-3'-yl)methyl]biphenyl-2-carboxylate The title compound was prepared by following the procedure for example 1, except that the reagent (2R)-6-hydroxyhexane-1,2-diyl dinitrate was replaced by (2R)-3-(2-hydroxyethoxy)propane-1,2-diyl dinitrate (intermediate 5), and 2-butyl-4-chloro-1-{[2'-(1-trityl-1H-tetrazol-5-yl)biphenyl-4-yl]methyl}-1H-imidazole-5-carboxylic acid was replaced by 4'-[(1,7'-dimethyl-2'-propyl-1H,3'H-2,5'-bibenzimidazol-3'-yl)methyl]biphenyl-2-carboxylic acid. $^1$H NMR (300 MHz, CDCl$_3$) δ 7.85 (m, 2H), 7.60-7.20 (m, 12H), 6.74 (q, 1H), 5.48 (s, 2H), 5.35 (m, 1H), 4.77 (m, 1H), 4.58 (m, 1H), 4.24 (t, 2H), 3.84 (s, 3H), 3.72 (m, 4H), 2.96 (t, 2H), 2.79 (s, 3H), 1.91 (m, 2H), 1.27 (d, 3H) 1.08 (t, 3H).

EXAMPLE 14

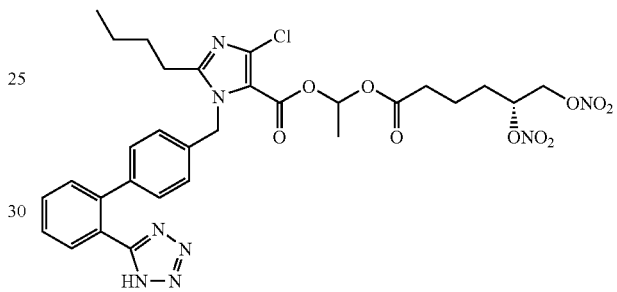

1-{[(5R)-5,6-bis(nitrooxy)hexanoyl]oxy}ethyl 2-butyl-4-chloro-1-{[2'-(1H-tetrazol-5-yl)biphenyl-4-yl] methyl}-1H-imidazole-5-carboxylate Step A: (5R)-5,6-bis(nitrooxy)hexanoic acid A mixture of (2R)-6-hydroxyhexane-1,2-diyl dinitrate (intermediate 2, 13.5 g, 60.2 mmol) and sodium periodate (38.74 g, 181 mmol) was suspended in water (250 mL)/acetonitrile (250 mL)/chloroform (250 mL). Ruthenium oxide hydrate (0.813 g, 6.11 mmol) was then added, turning the reaction into bright yellow. After 16 hours, the reaction mixture was concentrated in vacuo to remove the organic solvents. It was extracted with dichloromethane (3×200 mL), and the combined organic extracts were washed with brine, dried (magnesium sulfate), filtered, and concentrated in vacuo to afford the crude product. Chromatography over silica eluting with methanol/dichloromethane afforded (5R)-5,6-bis(nitrooxy) hexanoic acid as a yellow liquid. $^1$H NMR (500 MHz, CDCl$_3$) δ 5.25-5.35 (m, 1H), 4.76 (dd, J=3.1, 12.9 Hz, 1H), 4.49 (dd, J=6.4, 13.0 Hz, 1H), 2.4-2.5 (m, 2H), 1.7-1.9 (m, 4H).

Step B: 1-chloroethyl (5R)-5,6-bis(nitrooxy)hexanoate

To a dichloromethane (10 mL) solution of (5R)-5,6-bis (nitrooxy)hexanoic acid (292 mg, 1.22 mmol) was added oxalyl chloride (0.54 mL, 6.12 mmol), followed by a few drops of N,N-dimethylformamide. After bubbling has stopped, the reaction mixture was concentrated in vacuo to afford a yellow slurry, which was redissolved in dichloromethane (5 mL). This solution was added to a mixture of zinc chloride (166 mg, 1.22 mmol) and acetaldehyde (0.15 mL, 2.66 mmol) in dichloromethane (5 mL) at 0° C. The reaction mixture turned cloudy immediately. It was warmed up to room temperature, stirred for 1 hour, and concentrated in vacuo to afford the crude product. Chromatography over silica eluting with ethyl acetate/hexanes afforded the diastereomeric 1-chloroethyl (5R)-5,6-bis(nitrooxy)hexanoate as a colorless liquid. $^1$H NMR (500 MHz, CDCl$_3$) δ 6.54 (q, J=5.8 Hz, 1H, D1), 6.54 (q, J=5.8 Hz, 1H, D2), 5.25-5.35 (m, 1H), 4.76 (dd, J=3.1, 13.0 Hz, 1H, D1), 4.76 (dd, J=3.0, 12.8 Hz, 1H, D2), 4.49 (dd, J=6.5, 12.9 Hz, 1H, D1), 4.49 (dd, J=6.4, 13.1 Hz, 1H, D2), 2.4-2.5 (m, 2H), 1.7-1.9 (m, 7H).

Step C: 1-{[(5R)-5,6-bis(nitrooxy)hexanoyl]oxy}ethyl 2-butyl-4-chloro-1-{[2'-(1-trityl-1H-tetrazol-5-yl)biphenyl-4-yl]methyl}-1H-imidazole-5-carboxylate To a suspension of 2-butyl-4-chloro-1-{[2'-(1-trityl-1H-tetrazol-5-yl)biphenyl-4-yl]methyl}-1H-imidazole-5-carboxylic acid (intermediate 9, 815 mg, 1.20 mmol) and cesium carbonate (450 mg, 1.38 mmol) in N,N-dimethylformamide (5 mL) was added a N,N-dimethylformamide (5 mL) solution of 1-chloroethyl (5R)-5,6-bis(nitrooxy)hexanoate (361 mg, 1.20 mmol). It was then heated to 70° C. for 2 hours. Chromatography over silica eluting with ethyl acetate/hexanes afforded the diastereomeric 1-{[(5R)-5,6-bis(nitrooxy)hexanoyl]oxy}ethyl 2-butyl-4-chloro-1-{[2'-(1-trityl-1H-tetrazol-5-yl)biphenyl-4-yl]methyl}-1H-imidazole-5-carboxylate as a white solid. $^1$H NMR (500 MHz, CDCl$_3$) δ 7.88 (d, J=7.6 Hz, 1H), 7.50 (t, J=7.3 Hz, 1H), 7.45 (t, J=7.3 Hz, 1H), 7.32-7.36 (m, 4H), 7.22-7.30 (m, 6H), 7.10 (d, J=8.2 Hz, 2H), 6.96 (q, J=5.5 Hz, 1H), 6.94 (d, J=7.8 Hz, 6H), 6.79 (d, J=6.8 Hz, 2H), 5.52 (d, J=16.3 Hz, 1H, D1), 5.52 (d, J=16.3 Hz, 1H, D2), 5.37 (d, J=16.0 Hz, 1H, D1), 5.36 (d, J=16.2 Hz, 1H, D2), 5.18-5.25 (m, 1H), 4.66 (dd, J=2.3, 12.8 Hz, 1H, D1), 4.66 (dd, J=2.5, 12.8 Hz, 1H, D2), 4.38 (dd, J=6.1, 12.5 Hz, 1H, D1), 4.37 (dd, J=6.3, 12.7 Hz, 1H, D2), 2.50 (t, J=7.8 Hz, 2H), 2.28-2.32 (m, 2H), 1.58-1.78 (m, 6H), 1.51 (d, J=5.2 Hz, 3H), 1.27 (sextet, J=7.5 Hz, 2H), 0.85 (t, J=7.3 Hz, 3H); LC-MS: m/z 943 (M+H).

Step D: 1-{[(5R)-5,6-bis(nitrooxy)hexanoyl]oxy}ethyl 2-butyl-4-chloro-1-{[2'-(1H-tetrazol-5-yl)biphenyl-4-yl]methyl}-1H-imidazole-5-carboxylate A methanol (5 mL)/dichloromethane (5 mL) solution of 1-{[(5R)-5,6-bis(nitrooxy)hexanoyl]oxy}ethyl 2-butyl-4-chloro-1-{[2'-(1-trityl-1H-tetrazol-5-yl)biphenyl-4-yl]methyl}-1H-imidazole-5-carboxylate (713 mg, 0.756 mmol) was heated by microwave irradiation (120° C., 10 minutes). Purification of the reaction mixture by reversed-phase mass-directed high-performance liquid chromatography afforded the title compound. Chromatography of the diastereomeric mixture over Chiralpak AD-H, eluting with methanol/carbon dioxide, afforded the separate diastereomers.
D1: $^1$H NMR (500 MHz, CDCl$_3$) δ 8.03 (d, J=7.5 Hz, 1H), 7.60 (t, J=7.6 Hz, 1H), 7.54 (t, J=7.6 Hz, 1H), 7.42 (d, J=7.8 Hz, 1H), 7.16 (d, J=8.0 Hz, 2H), 6.96 (d, J=8.0 Hz, 2H), 6.95 (q, J=5.5 Hz, 1H), 5.54 (d, J=16.4 Hz, 1H), 5.47 (d, J=16.3 Hz, 1H), 5.18-5.24 (m, 1H), 4.70 (dd, J=3.0, 13.1 Hz, 1H), 4.42 (dd, J=6.4, 12.8 Hz, 1H), 2.65 (t, J=7.8 Hz, 2H), 2.32-2.42 (m, 2H), 1.66-1.80 (m, 6H), 1.56 (d, J=5.5 Hz, 3H), 1.36 (sextet, J=7.5 Hz, 2H), 0.89 (t, J=7.4 Hz, 3H); LC-MS: m/z 701 (M+H).
D2: $^1$H NMR (500 MHz, CDCl$_3$) δ 8.00 (d, J=7.4 Hz, 1H), 7.60 (t, J=7.6 Hz, 1H), 7.53 (t, J=7.6 Hz, 1H), 7.42 (d, J=7.6 Hz, 1H), 7.15 (d, J=8.0 Hz, 2H), 6.95 (d, J=8.7 Hz, 2H), 6.95 (q, J=5.5 Hz, 1H), 5.52 (d, J=16.5 Hz, 1H), 5.47 (d, J=16.5 Hz, 1H), 5.18-5.24 (m, 1H), 4.70 (dd, J=2.9, 13.0 Hz, 1H), 4.41 (dd, J=6.4, 12.8 Hz, 1H), 2.65 (t, J=7.8 Hz, 2H), 2.32-2.42 (m, 2H), 1.66-1.80 (m, 6H), 1.55 (d, J=5.5 Hz, 3H), 1.35 (sextet, J=7.5 Hz, 2H), 0.88 (t, J=7.4 Hz, 3H); LC-MS: m/z 701 (M+H).

EXAMPLE 15

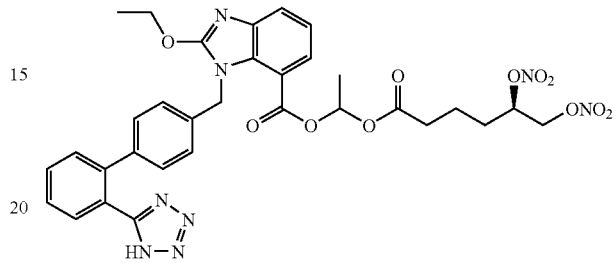

1-{[(5R)-5,6-bis(nitrooxy)hexanoyl]oxy}ethyl 2-ethoxy-1-{[2'-(1H-tetrazol-5-yl)biphenyl-4-yl]methyl}-1H-benzimidazole-7-carboxylate

Step A: 1-{[(5R)-5,6-bis(nitrooxy)hexanoyl]oxy}ethyl 2-ethoxy-1-{[2'-(1-trityl-1H-tetrazol-5-yl)biphenyl-4-yl]methyl}-1H-benzimidazole-7-carboxylate The title compound was prepared by following step C in example 14, except that the reagent 2-butyl-4-chloro-1-{[2'-(1-trityl-1H-tetrazol-5-yl)biphenyl-4-yl]methyl}-1H-imidazole-5-carboxylic acid was replaced by 2-ethoxy-1-{[2'-(1-trityl-1H-tetrazol-5-yl)biphenyl-4-yl]methyl}-1H-benzimidazole-7-carboxylic acid. $^1$H NMR (500 MHz, CDCl$_3$) δ 7.85 (d, J=7.5 Hz, 1H), 7.78 (d, J=7.8 Hz, 1H), 7.58 (d, J=8.1 Hz, 1H), 7.48 (t, J=7.3 Hz, 1H), 7.44 (t, J=7.6 Hz, 1H), 7.24-7.36 (m, 10H), 7.20 (t, J=7.9 Hz, 1H), 7.00 (d, J=8.2 Hz, 2H), 6.97 (q, J=5.5 Hz, 1H), 6.95 (d, J=7.8 Hz, 6H), 6.80 (d, J=7.8 Hz, 2H), 5.62 (d, J=16.2 Hz, 1H), 5.55 (d, J=16.2 Hz, 1H), 5.18-5.24 (m, 1H), 4.60-4.68 (m, 3H), 4.36 (dd, J=6.5, 13.1 Hz, 1H), 2.26-2.34 (m, 2H), 1.66-1.78 (m, 4H), 1.45 (t, J=7.1 Hz, 3H), 1.42 (d, J=5.5 Hz, 3H); LC-MS: m/z 969 (M+Na). Chromatography of the diastereomeric mixture over Chiralcel OD, eluting with isopropanol/heptane, afforded the separated diastereomers.

Step B: 1-{[(5R)-5,6-bis(nitrooxy)hexanoyl]oxy}ethyl 2-ethoxy-1-{[2'-(1H-tetrazol-5-yl)biphenyl-4-yl]methyl}-1H-benzimidazole-7-carboxylate The title compound was prepared by following step D in example 14, except that the reagent 1-{[(5R)-5,6-bis(nitrooxy)hexanoyl]oxy}ethyl 2-butyl-4-chloro-1-{[2'-(1-trityl-1H-tetrazol-5-yl)biphenyl-4-yl]methyl}-1H-imidazole-5-carboxylate was replaced by the individual diastereomerically pure 1-{[(5R)-5,6-bis(nitrooxy)hexanoyl]oxy}ethyl 2-ethoxy-1-{[2'-(1-trityl-1H-tetrazol-5-yl)biphenyl-4-yl]methyl}-1H-benzimidazole-7-carboxylate.
Diastereomer 1: $^1$H NMR (500 MHz, CDCl$_3$) δ 8.05 (dd, J=2.0, 6.7 Hz, 1H), 7.56-7.64 (m, 2H), 7.46 (t, J=7.6 Hz, 1H), 7.30 (d, J=6.6 Hz, 1H), 6.93-7.03 (m, 2H), 6.88 (d, J=8.0 Hz, 2H), 6.77 (d, J=7.6 Hz, 2H), 6.75 (q, J=5.5 Hz, 1H), 5.66 (d, J=16.9 Hz, 1H), 5.60 (d, J=16.9 Hz, 1H), 5.18-5.24 (m, 1H), 4.68 (dd, J=3.0, 13.1 Hz, 1H), 4.49 (qd, J=7.0, 9.8 Hz, 1H), 4.40 (dd, J=6.4, 13.0 Hz, 1H), 4.14-4.24 (m, 2H), 2.25-2.35 (m, 2H), 1.60-1.74 (m, 4H), 1.43 (t, J=7.1 Hz, 3H), 1.30 (d, J=5.5 Hz, 3H); LC-MS: m/z 705 (M+H).

Diastereomer 2: $^1$H NMR (500 MHz, CDCl$_3$) δ 8.04 (dd, J=1.8, 6.9 Hz, 1H), 7.56-7.64 (m, 2H), 7.44 (d, J=8.2 Hz, 1H), 7.30 (d, J=6.8 Hz, 1H), 6.93-7.03 (m, 2H), 6.87 (d, J=7.7 Hz, 2H), 6.76 (d, J=9.1 Hz, 2H), 6.74 (q, J=5.0 Hz, 1H), 5.65 (d, J=17.0 Hz, 1H), 5.60 (d, J=16.9 Hz, 1H), 5.17-5.21 (m, 1H), 4.67 (dd, J=3.0, 13.1 Hz, 1H), 4.48 (qd, J=7.3, 9.9 Hz, 1H), 4.40 (dd, J=6.4, 12.8 Hz, 1H), 4.14-4.24 (m, 2H), 2.25-2.35 (m, 2H), 1.60-1.74 (m, 4H), 1.42 (t, J=7.0 Hz, 3H), 1.29 (d, J=5.0 Hz, 3H); LC-MS: m/z 705 (M+H).

EXAMPLE 16

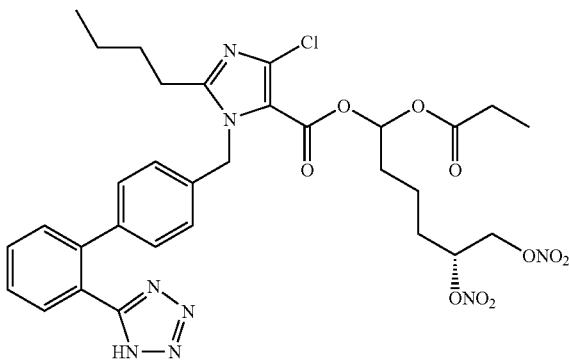

(5R)-5,6-bis(nitrooxy)-1-(propionyloxy)hexyl 2-butyl-4-chloro-1-{[2'-(1H-tetrazol-5-yl)biphenyl-4-yl]methyl}-1H-imidazole-5-carboxylate Step A: (2R)-6-oxohexane-1,2-diyl dinitrate Tetrapropylammonium perruthenate (16 mg, 0.05 mmol) was added to a dichloromethane (5 mL) solution of (2R)-6-hydroxyhexane-1,2-diyl dinitrate (intermediate 2, 105 mg, 0.49 mmol) and 4-methylmorpholine N-oxide (137 mg, 1.17 mmol). The solution was stirred at room temperature for 30 minutes. Water was added and the solution was extracted with dichloromethane. The combined organic layers were dried (magnesium sulfate), filtered, and concentrated in vacuo. Chromatography over silica eluting with ethyl acetate/hexanes afforded the title compound as a colorless oil. $^1$H NMR (500 MHz, CDCl$_3$) δ 9.79 (s, 1H), 5.25-5.32 (m, 1H), 4.76 (dd, J=13.0, 3.5 Hz, 1H), 4.49 (dd, J=13.0, 6.5 Hz, 1H), 2.59-2.54 (m, 2H), 1.83-1.73 (m, 4H).

Step B: (5R)-1-chloro-5,6-bis(nitrooxy)hexyl propionate

Zinc chloride (1.3 g, 9.54 mmol) was added to a dichloroethane (11.9 mL) solution of (2R)-6-oxohexane-1,2-diyl dinitrate (530 mg, 2.39 mmol) and propionyl chloride (0.23 mL, 2.62 mmol) at 0° C. The mixture was warmed to room temperature and stirred for 2 hours. Saturated aqueous sodium bicarbonate was added, and the solution was extracted with dichloromethane. The combined organic layers were dried (magnesium sulfate), filtered, and concentrated in vacuo. Chromatography over silica eluting with ethyl acetate/hexanes afforded the title compound as a colorless oil. $^1$H NMR (500 MHz, CDCl$_3$) δ 6.47 (d, J=5.0 Hz, 1H), 5.34-5.28 (m, 1H), 4.77 (dd, J=13.0, 3.5 Hz, 1H), 4.51 (dd, J=13.0, 6.5 Hz, 1H), 2.41 (q, J=7.5 Hz, 2H), 2.08 (q, J=7.5 Hz, 2H), 1.87-1.78 (m, 2H), 1.78-1.60 (m, 2H), 1.18 (t, J=7.5 Hz, 3H).

Step C: (5R)-5,6-bis(nitrooxy)-1-(propionyloxy)hexyl 2-butyl-4-chloro-1-{[2'-(1H-tetrazol-5-yl)biphenyl-4-yl]methyl}-1H-imidazole-5-carboxylate The title compound was prepared by following steps C and D in example 14, except that the reagent 1-chloroethyl (5R)-5,6-bis(nitrooxy)hexanoate was replaced by (5R)-1-chloro-5,6-bis(nitrooxy)hexyl propionate. $^1$H NMR (500 MHz, CDCl$_3$) δ 8.09-8.03 (m, 1H), 7.60 (t, J=7.5 Hz, 1H), 7.54 (t, J=7.5 Hz, 1H), 7.43 (d, J=7.5 Hz, 1H), 7.17 (d, J=7.5 Hz, 2H), 6.96 (d, J=7.5 Hz, 2H), 6.91 (t, J=5.0 Hz, 1H), 5.51 (q, J=16.5 Hz, 2H), 5.29 (ddd, J=13.0, 6.5, 3.0 Hz, 1H), 4.76 (dt, J=13.0, 3.5 Hz, 1H), 4.49 (dd, J=13.0, 6.5 Hz, 1H), 2.71 (t, J=8.5 Hz, 2H), 2.31 (q, J=7.5 Hz, 2H), 1.95-1.88 (m, 2H), 1.88-1.81 (m, 2H), 1.76-1.68 (m, 2H), 1.68-1.55 (m, 2H), 1.44-1.35 (m, 2H), 1.02 (t, J=7.5 Hz, 3H), 0.91 (t, J=7.5 Hz, 3H); LC-MS: m/z 716 (M+H).

EXAMPLE 17

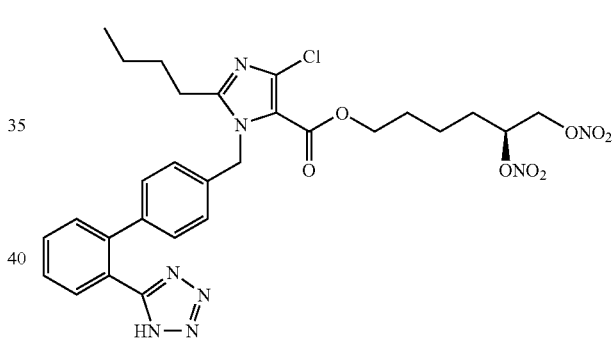

(5S)-5,6-bis(nitrooxy)hexyl 2-butyl-4-chloro-1-{[2'-(1H-tetrazol-5-yl)biphenyl-4-yl]methyl}-1H-imidazole-5-carboxylate To a dichloromethane (20 mL) solution of 2-butyl-4-chloro-1-{[2'-(1H-tetrazol-5-yl)biphenyl-4-yl]methyl}-1H-imidazole-5-carboxylic acid (1.76 g, 3.72 mmol), (2S)-6-hydroxyhexane-1,2-diyl dinitrate (intermediate 3, 0.83 g, 3.72 mmol), 1-ethyl-3-(3'-dimethylaminopropyl)carbodiimide hydrochloride (0.85 g, 4.46 mmol), and 1-hydroxybenzotriazole (0.68 g, 4.46 mmol) was added N-methylmorpholine (1.84 mL, 16.7 mmol), followed by N,N-dimethylaminopyridine (4.5 mg, 0.04 mmol). After 12 hours, the reaction mixture was washed with saturated sodium bicarbonate solution, brine, dried (magnesium sulfate), filtered, and concentrated in vacuo. Purification of the reaction mixture by reversed-phase mass-directed high-performance liquid chromatography afforded the title compound. $^1$H NMR (500 MHz, CD$_3$CN) δ 7.69 (d, J=7.6 Hz, 1H), 7.64 (t, J=7.6 Hz, 1H), 7.53 (t, J=7.7 Hz, 1H), 7.50 (d, J=7.8 Hz, 1H), 7.10 (d, J=8.2 Hz, 2H), 7.03 (d, J=8.0 Hz, 2H), 5.63 (s, 2H), 5.34-5.41 (m, 1H), 4.83 (dd, J=2.5, 12.8 Hz, 1H), 4.58 (dd, J=6.2, 13.0

Hz, 1H), 4.25 (t, J=6.2 Hz, 2H), 2.78 (t, J=7.8 Hz, 2H), 1.79 (q, J=7.5 Hz, 2H), 1.71 (quintet, J=6.8 Hz, 2H), 1.48-1.60 (m, 4H), 1.28 (sextet, J=7.4 Hz, 2H), 0.83 (t, J=7.3 Hz, 3H); LC-MS: m/z 643 (M+H).

EXAMPLE 18

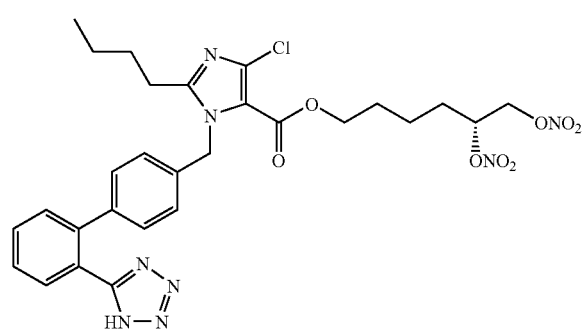

(5R)-5,6-bis(nitrooxy)hexyl 2-butyl-4-chloro-1-{[2'-(1H-tetrazol-5-yl)biphenyl-4-yl]methyl}-1H-imidazole-5-carboxylate The title compound was prepared by following the procedure for example 17, except that the reagent (2S)-6-hydroxyhexane-1,2-diyl dinitrate was replaced by (2R)-6-hydroxyhexane-1,2-diyl dinitrate (intermediate 2).

EXAMPLE 19

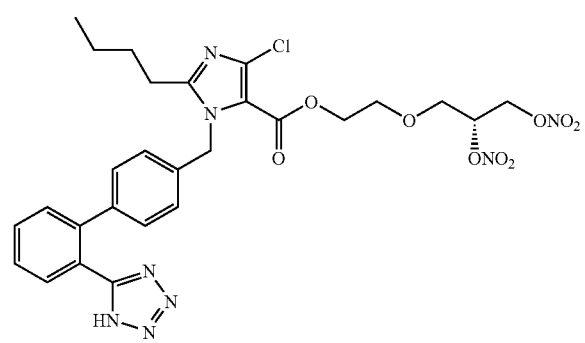

2-{[(2R)-2,3-bis(nitrooxy)propyl]oxy}ethyl 2-butyl-4-chloro-1-{[2'-(1H-tetrazol-5-yl)biphenyl-4-yl]methyl}-1H-imidazole-5-carboxylate The title compound was prepared by following the procedure for example 17, except that the reagent (2S)-6-hydroxyhexane-1,2-diyl dinitrate was replaced by (2R)-3-(2-hydroxyethoxy)propane-1,2-diyl dinitrate (intermediate 5). $^1$H NMR (500 MHz, CD$_3$CN) δ 7.72 (d, J=7.8 Hz, 1H), 7.65 (dt, J=1.1, 7.6 Hz, 1H), 7.55 (dt, J=1.0, 7.6 Hz, 1H), 7.52 (d, J=7.8 Hz, 1H), 7.10 (d, J=8.3 Hz, 2H), 6.99 (d, J=8.0 Hz, 2H), 5.54 (s, 2H), 5.44-5.52 (m, 1H), 4.82 (dd, J=3.1, 12.9 Hz, 1H), 4.68 (dd, J=6.8, 13.0 Hz, 1H), 4.32 (t, J=4.5 Hz, 2H), 3.66-3.84 (m, 4H), 2.59 (t, J=7.7 Hz, 2H), 1.58 (quintet, J=7.6 Hz, 2H), 1.31 (sextet, J=7.5 Hz, 2H), 0.86 (t, J=7.3 Hz, 3H); LC-MS: m/z 645 (M+H).

EXAMPLE 20

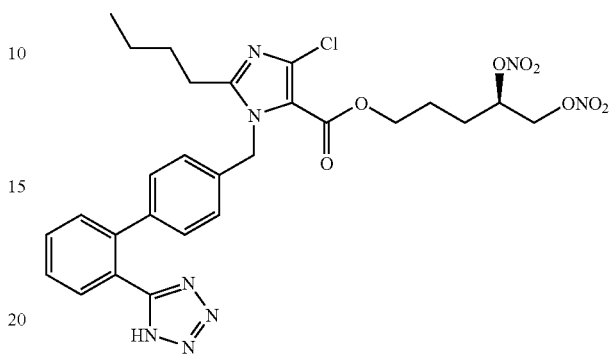

(4R)-4,5-bis(nitrooxy)pentyl 2-butyl-4-chloro-1-{[2'-(1H-tetrazol-5-yl)biphenyl-4-yl]methyl}-1H-imidazole-5-carboxylate The title compound was prepared by following the procedure for example 17, except that the reagent (2S)-6-hydroxyhexane-1,2-diyl dinitrate was replaced by (2R)-5-hydroxypentane-1,2-diyl dinitrate (intermediate 7). $^1$H NMR (500 MHz, CDCl$_3$) δ 7.83 (d, J=7.6 Hz, 1H), 7.58 (t, J=7.5 Hz, 1H), 7.49 (t, J=7.6 Hz, 1H), 7.41 (d, J=7.5 Hz, 1H), 7.08 (d, J=7.7 Hz, 2H), 6.87 (d, J=8.0 Hz, 2H), 5.50 (s, 2H), 5.28-5.40 (m, 1H), 4.74 (dd, J=2.9, 13.0 Hz, 1H), 4.48 (dd, J=6.2, 12.8 Hz, 1H), 4.22 (t, J=4.8 Hz, 2H), 2.53 (t, J=7.7 Hz, 2H), 1.74-1.96 (m, 4H), 1.58 (quintet, J=7.6 Hz, 2H), 1.28 (sextet, J=7.4 Hz, 2H), 0.83 (t, J=7.3 Hz, 3H); LC-MS: m/z 629 (M+H).

EXAMPLE 21

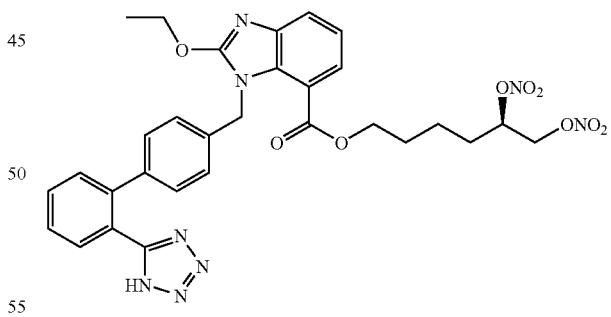

(5R)-5,6-bis(nitrooxy)hexyl 2-ethoxy-1-{[2'-(1H-tetrazol-5-yl)biphenyl-4-yl]methyl}-1H-benzimidazole-7-carboxylate The title compound was prepared by following the procedure for example 18, except that the reagent 2-butyl-4-chloro-1-{[2'-(1H-tetrazol-5-yl)biphenyl-4-yl]methyl}-1H-imidazole-5-carboxylic acid was replaced by 2-ethoxy-1-{[2'-(1H-tetrazol-5-yl)biphenyl-4-yl]methyl}-1H-benzimidazole-7-carboxylic acid. $^1$H NMR (500 MHz, CD$_3$CN) δ 7.75 (d, J=7.5 Hz, 1H), 7.63 (t, J=7.6 Hz, 1H), 7.57 (t, J=7.6 Hz, 1H), 7.47 (d, J=7.8 Hz, 1H), 7.42 (d, J=7.8 Hz, 1H), 7.32 (d, J=7.8 Hz, 1H), 7.08 (t, J=7.9 Hz, 1H), 6.94 (d, J=7.5 Hz, 2H), 6.85 (d, J=7.7 Hz, 2H), 5.53 (s, 2H), 5.28-5.34 (m, 1H), 4.77 (dd, J=1.4, 12.9 Hz, 1H), 4.53 (dd, J=6.0, 12.8 Hz, 1H), 4.44 (q, J=7.0 Hz, 2H), 4.08 (t, J=6.2 Hz, 2H), 1.72 (q, J=7.4 Hz, 2H), 1.60 (quintet, J=7.1 Hz, 2H), 1.46 (quintet, J=7.4 Hz, 2H), 1.41 (t, J=7.1 Hz, 3H); LC-MS: m/z 647 (M+H).

EXAMPLE 22

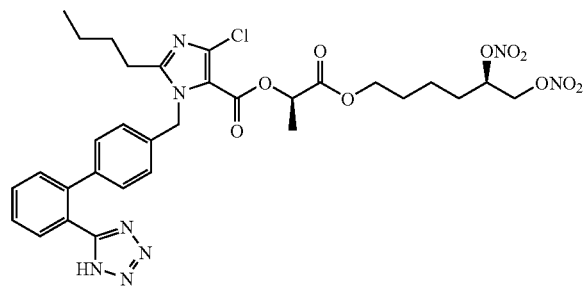

(1R)-2-{[(5R)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate Step A: (1R)-2-(benzyloxy)-1-methyl-2-oxoethyl 2-butyl-4-chloro-1-{[2'-(1H-tetrazol-5-yl)biphenyl-4-yl]methyl}-1H-imidazole-5-carboxylate The title compound was prepared by following the procedure for example 17, except that the reagent (2S)-6-hydroxyhexane-1,2-diyl dinitrate was replaced by D-lactic acid benzyl ester. $^1$H NMR (500 MHz, CDCl$_3$) δ 8.09 (d, J=7.5 Hz, 1H), 7.58 (t, J=7.5 Hz, 1H), 7.53 (t, J=7.5 Hz, 1H), 7.40 (d, J=7.0 Hz, 1H), 7.32-7.24 (m, 5H), 7.13 (d, J=8.0 Hz, 2H), 6.93 (d, J=8.0 Hz, 2H), 5.47 (dd, J=26.0, 16.0 Hz, 2H), 5.19 (q, J=7.0 Hz, 1H), 5.11 (s, 2H), 2.69 (t, J=8.0 Hz, 2H), 1.72 (quintet, J=7.5 Hz, 2H), 1.55 (d, J=7.0 Hz, 3H) 1.39 (sextet, J=7.5 Hz, 2H), 0.91 (t, J=7.5 Hz, 3H); LCMS (M+H) found 599.2.

Step B: (2R)-2-{[(2-butyl-4-chloro-1-{[2'-(1H-tetrazol-5-yl)biphenyl-4-yl]methyl}-1H-imidazol-5-yl)carbonyl]oxy}propanoic acid 10% Palladium on carbon (59 mg, 0.55 mmol) was added to a stirred ethanol (5.5 mL) solution of (1R)-2-(benzyloxy)-1-methyl-2-oxoethyl 2-butyl-4-chloro-1-{[2'-(1H-tetrazol-5-yl)biphenyl-4-yl]methyl}-1H-imidazole-5-carboxylate. The mixture was stirred under hydrogen for 2 hours. The mixture was filtered through Celite, and the filtrate was concentrated in vacuo to give the title compound as a white solid. $^1$H NMR (500 MHz, CDCl$_3$) δ 7.67-7.62 (m, 2H), 7.56-7.50 (m, 2H), 7.09 (d, J=8.0 Hz, 2H), 7.01 (d, J=8.0 Hz, 2H), 6.87 (q, J=5.5 Hz, 1H), 5.67 (d, J=16.5 Hz, 1H), 5.57 (d, J=16.5 Hz, 1H), 5.15 (q, J=6.5 Hz, 1H), 2.65 (t, J=7.5 Hz, 2H), 1.56 (quintet, J=7.5 Hz, 6H), 1.49 (d, J=7.0 Hz, 3H), 1.31 (sextet, J=7.5 Hz, 2H), 0.87 (t, J=7.5 Hz, 3H); LCMS (M+H) found 509.2.

Step C: (1R)-2-{[(5R)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate The title compound was prepared by following the procedure for example 17, except that the reagent 2-butyl-4-chloro-1-{[2'-(1H-tetrazol-5-yl)biphenyl-4-yl]methyl}-1H-imidazole-5-carboxylic acid was replaced by (2R)-2-{[(2-butyl-4-chloro-1-{[2'-(1H-tetrazol-5-yl)biphenyl-4-yl]methyl}-1H-imidazol-5-yl)carbonyl]oxy}propanoic acid. $^1$H NMR (500 MHz, CDCl$_3$) δ 7.68-7.63 (m, 2H), 7.57-7.51 (m, 2H), 7.10 (d, J=8.0 Hz, 2H), 7.00 (d, J=8.0 Hz, 2H), 5.66 (d, J=16.5 Hz, 1H), 5.57 (d, J=16.5 Hz, 1H), 5.34 (ddd, J=13.5, 6.0, 2.5 Hz, 1H), 5.16 (q, J=7.0 Hz, 1H), 4.85-4.82 (m, 1H), 4.53 (dd, J=13.0, 6.5, Hz, 1H), 4.22-4.10 (m, 2H), 2.66 (t, J=7.7 Hz, 2H), 1.76-1.70 (m, 2H), 1.67 (quintet, J=7.0 Hz, 2H), 1.57 (p, J=7.7 Hz, 2H), 1.48 (d, J=7.0 Hz, 3H), 1.32 (sextet, J=7.5 Hz, 2H), 0.87 (t, J=7.5 Hz, 3H); LCMS (M+H) found 715.2.

The following examples can be prepared by following the procedure for example 22 using the appropriate α-hydroxycarboxylic acid benzyl esters in step B and dinitrate alcohol in step C:

TABLE 1

| Example | Name | Structure | HPLC-mass spectrum m/e |
|---|---|---|---|
| 23 | (1S)-2-{[(5R)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate | 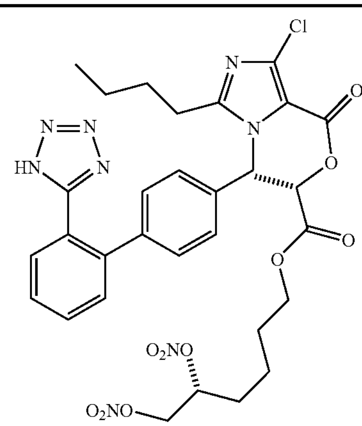 | 715 (M + H) |

TABLE 1-continued

| Example | Name | Structure | HPLC-mass spectrum m/e |
|---|---|---|---|
| 24 | (1R)-2-{[(5S)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate | 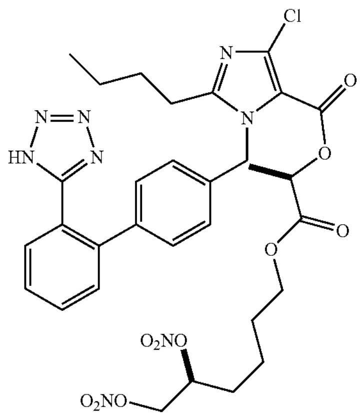 | 715 (M + H) |
| 25 | (1S)-2-{[(5S)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate | 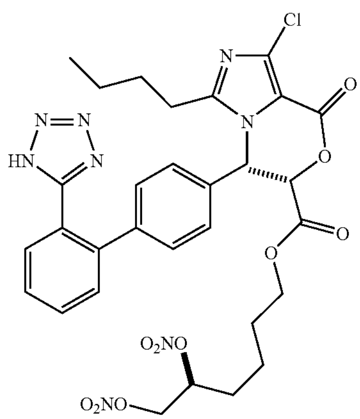 | 715 (M + H) |
| 26 | (1S)-2-{[(5S)-5,6-bis(nitrooxy)hexyl]oxy}-1-methyl-2-oxoethyl 2-butyl-4-chloro-1-{[2'-(1H-tetrazol-5-yl)biphenyl-4-yl]methyl}-1H-imidazole-5-carboxylate | 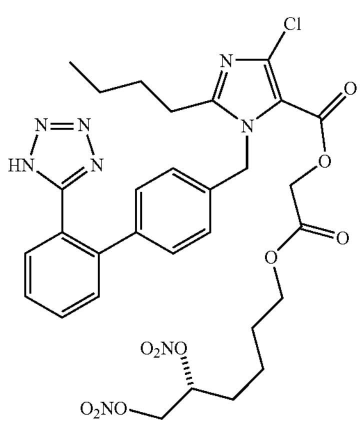 | 701 (M + H) |

DATA TABLE 1(CONTINUED)

| Structure | Compound Number | EC$_{50}$ in vessel relaxation assay |
|---|---|---|
| 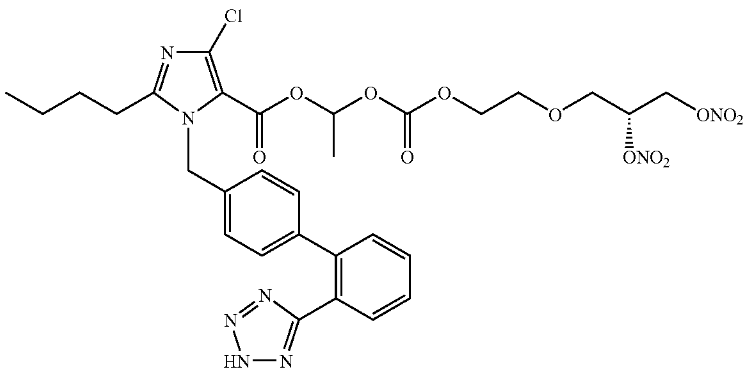 | Example 3 | 5.0 μM |
| 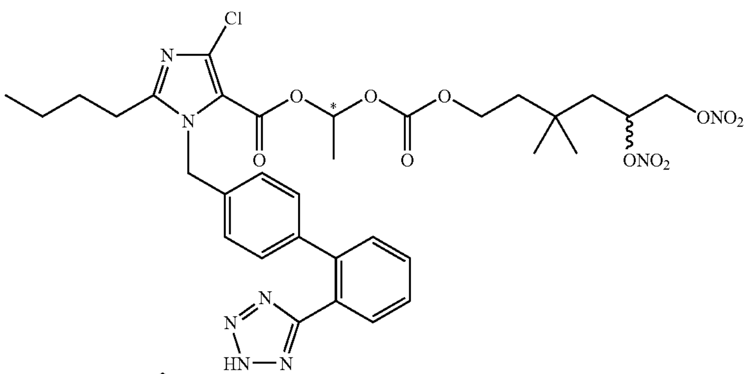 | Example 4 | 1.1 μM |
| 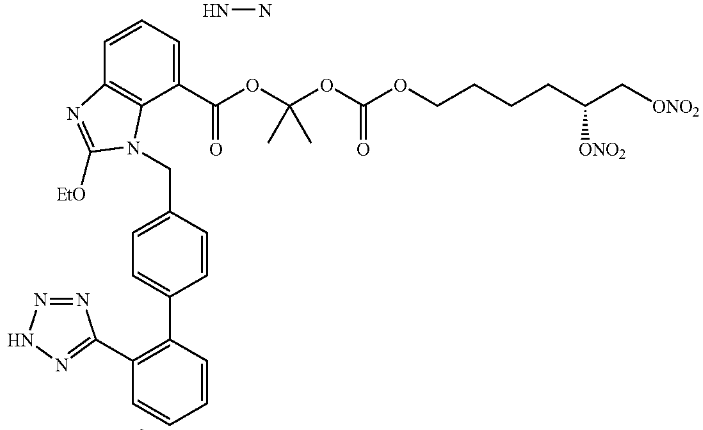 | Example 9 | 0.99 μM |
| 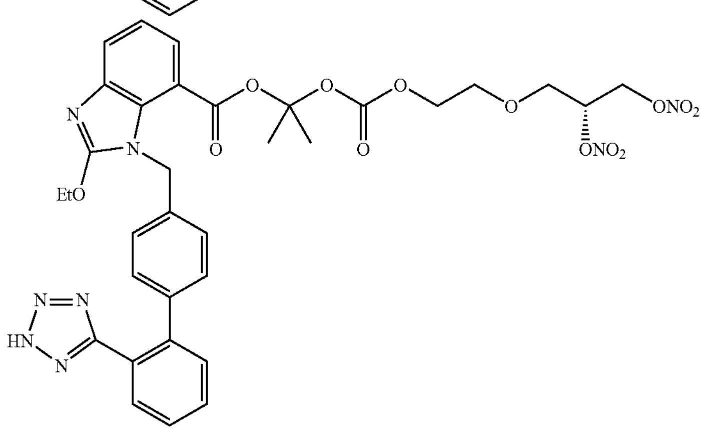 | Example 11 | 2.3 μM |

DATA TABLE 1(CONTINUED)-continued

| Structure | Compound Number | EC$_{50}$ in vessel relaxation assay |
|---|---|---|
| 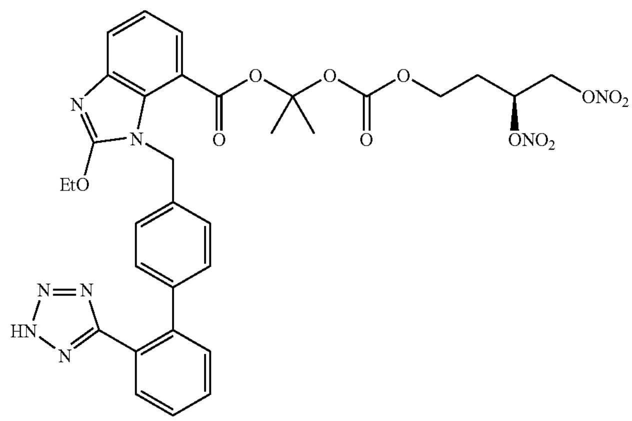 | Example 12 | 3.73 μM |
| 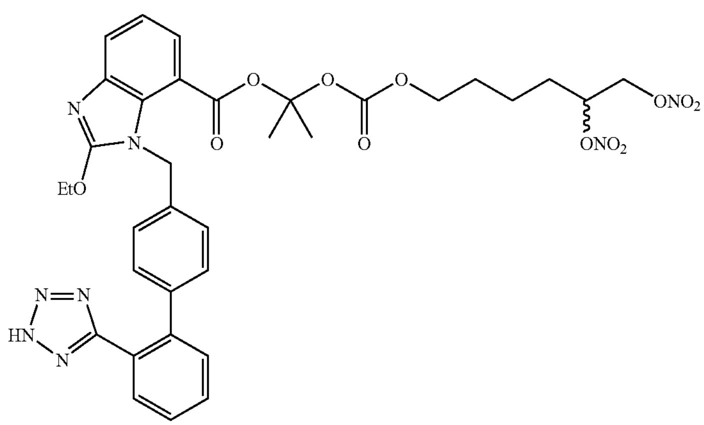 | Example 8 | 0.37 μM |
| 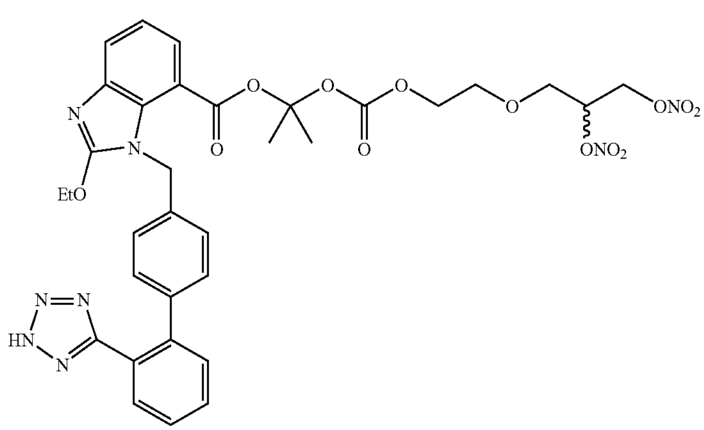 | Example 10 | 2.38 μM |

What is claimed is:

1. A compound having the following formula:

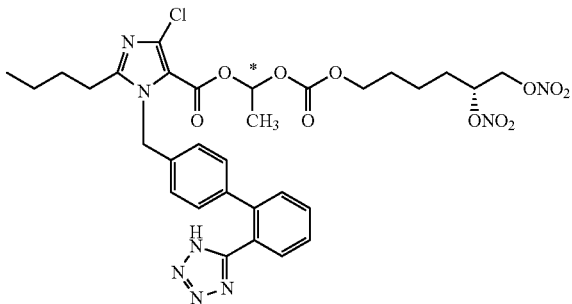

or a pharmaceutically acceptable salt of the compound.

2. A compound of claim 1, or a pharmaceutically acceptable salt thereof, selected from the group consisting of
1-[({[(5R)-5,6-bis(nitrooxy)hexyl]oxy}carbonyl)oxy] ethyl 2-butyl-4-chloro-1-{[2'-(1H-tetrazol-5-yl)biphenyl-4-yl]methyl}-1H-imidazole-5-carboxylate—Diastereomer A, and
1-[({[(5R)-5,6-bis(nitrooxy)hexyl]oxy}carbonyl)oxy] ethyl 2-butyl-4-chloro-1-{[2'-(1H-tetrazol-5-yl)biphenyl-4-yl]methyl}-1H-imidazole-5-carboxylate—Diastereomer B.

3. A compound of claim 2, or a pharmaceutically acceptable salt thereof, which is
1-[({[(5R)-5,6-bis(nitrooxy)hexyl]oxy}carbonyl)oxy] ethyl 2-butyl-4-chloro-1-{[2'-(1H-tetrazol-5-yl)biphenyl-4-yl]methyl}-1H-imidazole-5-carboxylate—Diastereomer A.

4. A pharmaceutical composition comprising a compound of claim 1 and a pharmaceutically acceptable carrier.

5. A pharmaceutical composition comprising a compound of claim 1, a diuretic, and a pharmaceutically acceptable carrier.

6. A pharmaceutical composition comprising a compound of claim 3 and a pharmaceutically acceptable carrier.

7. A pharmaceutical composition comprising a compound of claim 3, a diuretic, and a pharmaceutically acceptable carrier.

* * * * *